United States Patent
Inostroza Silva et al.

(10) Patent No.: US 10,648,893 B2
(45) Date of Patent: May 12, 2020

(54) METHOD, SYSTEMS AND KIT FOR FORENSIC IDENTIFICATION, POST MORTEM INTERVAL ESTIMATION AND CAUSE OF DEATH DETERMINATION BY RECOVERY OF DENTAL TISSUE IN PHYSIOLOGICAL CONDITIONS

(71) Applicant: UNIVERSIDAD DE LOS ANDES, Las Condes, Santiago (CL)

(72) Inventors: Carolina Inostroza Silva, Santiago (CL); Patricio Carrasco Tapia, Santiago (CL)

(73) Assignee: UNIVERSIDAD DE LOS ANDES, Santiago (CL)

( * ) Notice: Subject to any disclaimer, the term of this patent is extended or adjusted under 35 U.S.C. 154(b) by 245 days.

(21) Appl. No.: 14/893,328

(22) PCT Filed: May 20, 2014

(86) PCT No.: PCT/IB2014/061568
§ 371 (c)(1),
(2) Date: Nov. 23, 2015

(87) PCT Pub. No.: WO2014/188345
PCT Pub. Date: Nov. 27, 2014

(65) Prior Publication Data
US 2016/0123853 A1 May 5, 2016

Related U.S. Application Data

(60) Provisional application No. 61/826,558, filed on May 23, 2013.

(51) Int. Cl.
| | | |
|---|---|---|
| C12Q 1/68 | (2018.01) | |
| G01N 1/30 | (2006.01) | |
| A61B 5/1178 | (2016.01) | |
| A01N 1/00 | (2006.01) | |
| G01N 1/08 | (2006.01) | |
| G01N 1/36 | (2006.01) | |
| G01N 1/00 | (2006.01) | |
| G01N 23/04 | (2018.01) | |

(52) U.S. Cl.
CPC .............. *G01N 1/30* (2013.01); *A01N 1/00* (2013.01); *A61B 5/1178* (2013.01); *G01N 1/08* (2013.01); *G01N 1/36* (2013.01); *G01N 23/04* (2013.01); *G01N 2001/007* (2013.01); *G01N 2223/612* (2013.01)

(58) Field of Classification Search
None
See application file for complete search history.

(56) References Cited

U.S. PATENT DOCUMENTS

| 6,329,149 B1 | 12/2001 | Cobb |
| 6,767,740 B2 | 7/2004 | Sramek et al. |
| 2004/0126796 A1 | 7/2004 | Carlson et al. |

OTHER PUBLICATIONS

Garcia et al. (Cient Dent vol. 7 2010 p. 9-13).*
Shemesh et al. (JOE 2011 vol. 37 p. 513) (Year: 2011).*
Silva et al., "Use of DNA Technology in Forensic Dentistry", J. Appl. Oral Sci., vol. 15, No. 3, 2007, pp. 156-61.
Kvaal et al., "Age estimation of adults from dental radioagraphs". Forensic Science International, vol. 74,1995, pp. 175-185.
Sweet et al., "DNA Analysis of Dental Pulp to Link Incinerated Remains of Homicide Victim to Crime Scene", Journal of Forensic Sciences, vol. 40, No. 2, Mar. 1995, pp. 310-314.
Corte-Real et al. "The DNA extraction from the pulp dentine complex of both with and without carious", International Congress Series vol. 1288, 2006, pp. 710-712.
Higgins et al. "Teeth as a source of DNA for forensic identification of human remains: A Review", Science and Justice 53, 2013, pp. 433-441.
International Search Report and Written Opinion, dated Jan. 5, 2016; PCT/IB2014/061568 (7 pages).
Jiang et al., "Telomere shortening and ageing", Z Gerontol Geriat 40, 2007, pp. 314-324.
Sweet et al., "Recovery of DNA from human teeth by cryogenic grinding", J. Forensic Sci., 1998, pp. 1199-1202.
Gilbert et al., "Distribution patterns of postmortem damage in human mitochondrial DNA", Am. J. Hum. Genet. 72, 2003, pp. 32-47.
Woodward et al., "Amplification of Ancient Nuclear DNA from teeth and soft tissues", PCR Methods and Applications 3, 1994, pp. 244-247, downloaded from genome.cshlp.org on Apr. 6, 2016.
Tran-Hung et al., "A new method to extract dental pulp DNA: application to universal detection on bacteria", Plos One 10, e1062, 2007, pp. 1-8.
Alonso et al., "Challenges of DNA profiling in mas disaster investigations", Croat. Med. J. 46 (4), 2005, pp. 540-548.
Malaver et al., "Different dental tissues as source of DNA for human identification in forensic cases", Croat. Med J. 44(3), 2003, pp. 306-309.
Ricaut et al., "STR-genotyping from human medieval tooth and bone samples", Forensic Sci. Int. 151 (1), 2005, pp. 31-35.

(Continued)

*Primary Examiner* — Katherine D Salmon
(74) *Attorney, Agent, or Firm* — Procopio, Cory, Hargreaves & Savitch LLP

(57) ABSTRACT

The present invention is related to a method for obtaining dental pulp and root cement in the forensic dentistry field, wherein the method comprises the steps of: (a) obtaining a tooth; (b) taking a digital radiography to the tooth; (c) external rehydrating of the tooth; (d) perforating the rehydrated tooth; (e) internal rehydrating of dentin pulp complex (f) obtaining rehydrated root cement; (g) obtaining rehydrated dental pulp content with a low speed rotation tool; and (h) storing, preservation, processing and/or analyses of the rehydrated dental pulp content and rehydrated root cement, and the use of this method and kits thereof for forensic identification, estimation of post mortem interval (early and late) and determination of possible causes of death.

25 Claims, 12 Drawing Sheets

(56) References Cited

OTHER PUBLICATIONS

Vavpotič et al., "Charactersitics of the number of odontoblasts in human dental pulp post-mortem", Forensic Sci Int. 193, 2009, pp. 122-126.

Caballín et al., "Evaluation of histological pulp changes for determining the time since death", (Original title: Valoración de los cambios histológicos pulpares para la determinación de la data de la muerte), Cient. Dent. 7(1) 2010 pp. 9-13.

Tilotta et al., "A comparative study of two methods of dental pulp extraction for genetic fingerprinting", Forensic Science International 202 (1-3), 2010, pp. e39-e43.

Pinchi et al., "Techniques of dental DNA extraction: Some operative experiences", Forensic Science International 204 (1-3), 2011, pp. 111-114.

Vasiliadis, et al., "Translucent root dentine in relationship to increasing age: review of the literature", Research Journal of Biological Sciences 6 (2), ISSN: 1815-8846, 2011, pp. 92-95.

Goedbloed et al., "Comprehensive mutation analysis of 17 Y-chromosomal short tandem repeat polymorphisms included in the AmpFISTR® Yfiler® PCR amplification kit", Int J. Legal Med. 123, 2009, pp. 471-482.

Ruiz Linares et al., "Geographic clustering of human Y-chromosome haplotypes", Ann. Hum. Genet. 60, 1996, pp. 401-408.

Roewer et al., "Online reference database of European Y-chromosomal short tandem repeat (STR) haplotypes", Forensic Sci. Int. 118, 2001, pp. 106-113.

Tasaki et al., "Age estimation in dental pulp DNA based on human telomere shortening", Int J Legal Med 117, 2003, pp. 232-234.

Rees et al., "Genetics of hair and skin color", Annu. Rev. Genet. 37, 2003, pp. 67-90.

Valverde et al., "Variants of the melanocyte-stimulating hormone receptor gene are associated with red hair and fair skin in humans", Nat. Genet. 11, 1995, pp. 328-330.

Kayser et al., "Three Genome-wide Association Studies and a Linkage Analysis Identify HERC2 as a Human Iris Color Gene", The American Journal of Human Genetics 82,2008, pp. 411-423.

Sturm et al., "Genetics of human iris colour and patterns", Pigment Cell Melanoma Res. 22, 2009, pp. 544-562.

Star et al., "Human dental age estimation by calculation of pulp-tooth volume ratios yielded on clinically acquired cone beam computed tomography images of monoradicular teeth", J. Forensic Sci. vol. 56, No. S1, 2011, pp. S77-S82.

Pellegrini et al., "Development and validation of a gas chromatography—mass spectrometry assay for opiates and cocaine in human teeth", Journal of Pharmaceutical and Biomedical Analysis 40, 2006, pp. 662-668.

Arayne et al., "Simultaneous determination of metformin, cimetidine, famotidine, and ranitidine in human serum and dosage formulations using HPLC with UV detection", Journal of Chromatographic Science, vol. 48, 2010, pp. 721-725.

Black et al., "C-reactive Protein", The Journal of Biological Chemistry, vol. 279, No. 47, 2004, pp. 48487-48490.

https://www.analytik-jena.de/en/analytical-instrumentation/products/atomic-absorption-spectrometry/flame-graphite-furnace-technique/zeenit-700-p.html; printed May 12, 2016; 2 pages.

Luna Maldonado "The data of death, an unresolved challenge", (Original title: La data de la muerte, un desafio no resulto), Rev. Esp. Med. Legal, 2010, 36 (2), pp. 47-48.

Smith et al., "A systematic approach to the sampling of dental DNA", J. Forensic Sci., vol. 38, No. 5, Sep. 1993, Abstract.

Yamamoto et al., "Analysis of DNA from tooth and application to forensic dental medicine", Nihon Hoigaku Zasshi, vol. 4, No. 5, Oct. 1989, Abstract.

Carrasco et al., Obtaining of DNA from dental pulps with forensic purposes. Use of AMP-FLP technique specific for APO-B locus. (Original title: Obtención de ADN de pulpas dentarias con fines de identificación médico legal. Aplicación de la técnica AMP-FLP específica para el locus APO-B), Santiago: Dentistry Faculty, University of Chile; 1993.

Carrasco et al., Contributions of forensic dentistry to forensic and criminological identification. Use of DNA from buccal dental tissues and fluids in forensic identification. (Original title: Aportes de la odontología forense a la identificación médico legal y criminalística. Utilización de ADN de tejidos y fluidos buco dentarios en identificación médico legal), Ediciones Jurídicas de Santiago, Santiago, Chile, 2012.

Carrasco et al., "Thanatological forensic approach to oral maxillofacial territory, proposing a technique", (Original title: Abordaje médico legal tanatológico al territorio buco maxilofacial, proposición de una técnica), Santiago: Dentistry Faculty, University of Chile, 1992.

Pretty, I. A., "Forensic Dentistry: 1. Identification of human remains" Dent Update, Dic; 34 (10), 2007, Abstract.

Lijnen et al., "DNA research in forensic dentistry", Methods Find Exp Clin Pharmacol. vol. 23, No. 9, Nov. 2001, Abstract.

Diwaker et al., "DNA fingerprinting. The future of forensic dentistry—a review", Indian J Dent Res., vol. 12, No. 2, Jun. 2001, Abstract.

Henssge, C., "Death time estimation in case work. I. The rectal temperature time of death nomogram", Forensic Sci Int., vol. 38, No. 3-4, Sep. 1988, Abstract.

Boy et al., "Case Report Flow Cytometric Evaluation of Postmortem Pulp DNA Degradation" American Journal of Forensic Medicine & Pathology, vol. 24, 2003, Abstract.

Ohira et al., "Advantages of dental mitochondrial DNA for detection and classification of the sequence variation using restriction fragment length polymorphisms", American Journal of Forensic Medicine and Pathology, vol. 20, No. 3, Sep. 1999.

\* cited by examiner

METHOD, SYSTEMS AND KIT FOR FORENSIC IDENTIFICATION, POST MORTEM INTERVAL ESTIMATION AND CAUSE OF DEATH DETERMINATION BY RECOVERY OF DENTAL TISSUE IN PHYSIOLOGICAL CONDITIONS

TECHNICAL FIELD

The present invention is related to the field of forensic dentistry and criminalistics, specifically related to systems and methods for the forensic identification process, estimation of post mortem interval for early and late post mortem interval and determination of cause of death.

The genomic DNA and profiling service provided by the present invention allows individuals to obtain a record of their genetic profile, a unique combination of gene markers found in their DNA that serves as a unique genetic ID.

BACKGROUND ART

The forensic unknowns that need to be answered before a legal and forensic medical case involving human remains are: species, number of individuals, racial tendency, gender, age, and identity (genetic profile) Post mortem interval and cause of death are also two very important unknowns to be estimated. Each of these aspects has been studied by the forensic sciences, and in the last 20 years the laboratory examinations with strong scientific evidence have become more important in forensic and criminological examinations.

DNA profiles and phenotypic profile, allows to answer a large number of forensic unknowns, discriminate species and number of individuals, racial tendency, gender, age (by studying the telomeres of gDNA[1]), and individual characteristics (size, diseases, eye color, etc.). Elsewhere, gene expression profiling is a technique used in molecular biology to query the expression of thousands of genes simultaneously. In the context of cancer and diseases, gene expression profiling has been used to more accurately classify tumors. The information derived from gene expression profiling often has an impact on predicting the patient's clinical outcome.

From a forensic and criminological point of view, the possibility of improving the methods and laboratory techniques is always an objective; most effectiveness in laboratory techniques allows more accuracy and therefore more useful results for research. In addition, from a social point of view improvement of these methodologies contributes in more accurate and quick forensic examinations.

1. Forensic and Criminological Aspects and Limitations:
    Most gDNA extraction protocols using teeth (forensic odontology), completely destroy the tooth, therefore the loss of evidence (tooth) in any forensic laboratory process, is always a difficulty, since it is not possible to repeat the process or perform new examinations in front of a doubt.
    The estimation of post mortem interval may allow solving crimes by locating the victim and the killer at a time and place, discarding presented alibis, and relating time with cause of death, etc. These aspects have been very little studied by forensic dentistry, and the contribution that the teeth could make for determining cause of death has also not been studied in depth.
    Determination of cause of death is a forensic unknown little studied, as well as determination of individual characteristics (phenotypic profiles, diseases etc.)

1. Social Aspect:
    Disasters as plane crashes, fires, explosions, earthquakes, tsunamis and others can determine have little evidence to examine and that once the analysis is completed, these samples are the only remains possible to deliver to relatives, so the loss of them in the process of obtaining the genetic profile or other, is a problem which brings more suffering to the affected family.
    For example, in these cases may be technically feasible to initiate a DNA-led identification programme. The scale of DNA led programmes can range from a local incident, involving only a few individuals, to programmes attempting to identify tens of thousands of individuals. The two largest DNA-led programmes to date have helped to identify thousands of individuals killed in the Balkans between 1991 and 2000, and approximately 1,700 individuals killed in the September 2001 attack on the World Trade Center in New York, USA. In Chile, according to statistics provided by the biochemical unit of the criminological laboratory (Lacrim) of the Chilean Investigative Police (PDI) this unit attends an average of 1,200 requests for identification examinations per year, which generate 12,000 biological samples for obtaining genetic profiles. 50% of these requests are homicides and the other 50% is divided between sexual offenses, robberies and other (finding of bodies or human remains, natural disasters, fires, etc.).
    Therefore, the problem is that current methods for determining forensic genetic profile destroy the tooth, thus destroying the evidence and also the possibility of using the piece for further physical or biochemical analyses. This is especially crucial when the tooth is one of the few (if not the only) evidence that can generate any type of information, as in explosions, fires or corpses being long term dead.
    Obtaining gDNA from human tissues has been intense developed over the past 20 years, since it allows to address several of the forensic unknowns described above (species, number of individuals, racial tendency, gender, age (by studying the telomeres), identity (genetic profile), individual characteristics, post mortem interval and cause of death.
    For obtaining the genetic profile of a victim to be identified, fluids (blood, saliva, semen, etc.), soft tissue (skin, muscle, hair, nails, etc.) or hard tissues (bone and teeth) are typically used. On the other hand the study of changes in corpses and action of cadaveric fauna, can estimate post mortem interval, i.e. the time between death and the discovery of the body. Determination of cause of death is also affected or hindered by the processes of cadaveric transformation and the passage of time.
    Post mortem interval and cause of death can affect the integrity and preservation of the DNA structure (fragmentation, degradation, contamination) and it is difficult to obtain it from fluids and soft tissues, but not from hard tissues which allow obtaining this macromolecule despite the time elapsed. Teeth are as a vault, which helps maintaining a more stable and free of external contamination DNA, independent of environmental factors and time elapsed. The pulp, a loose connective tissue located inside the pulp chamber in the center of the tooth, is one of the best sources of gDNA of the tooth. The root cement, the mineralized cellular tissue (cementocytes) covering the outside of the root of the tooth, can also be used for gDNA obtaining.
    The most used method for obtaining tooth gDNA for forensic identification purposes comprises the destruction (pulverization) of the sample, allowing obtaining cellular remains or gDNA traces useful for determining genetic profile. This determines the total loss of the sample or a high potential for contamination that preclude the use of dental tissues for other analysis (post mortem interval and cause of death). The disadvantage of this method is that given the high degree of handling, there is a greater possibility of contamination of the gDNA obtained.[2, 3]

Research in this area[4, 5, 6, 7, 8, 9] have attempted to develop other methods for obtaining pulp gDNA not necessarily mean total destruction of the tooth sample with the aim of minimizing handling and contamination by longitudinal cut techniques, immobilization of the tooth in acrylic matrix, enzyme injection to the pulp chamber, high speed rotary instruments use, etc. Tran-Hung et al.[8] were able to obtain pulp samples from 5 years corpses, taken from sectioned teeth, achieving only 25% success in obtaining gDNA from these pieces.

Loss in the structure and morphology of the pulp chamber and therefore of the dental pulp occurs by destroying or sectioning the tooth, preventing evaluation of morphological, cytological and histological changes of the pulp or gDNA degradation with time, which allow to estimate post mortem interval and cause of death.

Forensic dentistry has placed emphasis on obtaining and extraction of gDNA from teeth to achieve identity, but has neglected the contribution that the dental pulp can make in the estimation of post mortem interval and determination of cause of death.

There is a wide range of signs in corpses for estimation of early post mortem interval, (rigor mortis, presence of lividities, cooling, green cecal patches, cadaveric entomofauna, etc.). The problem arises in the more advanced stages of the destructive process and more specifically at the stage of bones of the remains, since it is no longer possible to use the degradation of soft tissues as a parameter and cadaveric entomofauna could not always deliver accurate information by itself, since it is affected by environmental conditions.

The destruction of the dental pulp and root cement (or not using them) also prevents toxicological studies of this tissue, which can determine possible causes of death (presence of traces of pesticides, heavy metals, poisons, drugs and drug abuse) or give pharmacological information on aspects related to systemic conditions (diabetes, hypertension, cancer, etc.) that can help with identification and characterization.

In short, forensic dentistry faces the following problems:
1. In some methods, excessive handling[2, 8] involves contamination of the sample.
2. Use of high speed rotary instruments for recovering the dental pulp content or remains causes temperature increase, accelerating degradation of the pulp remains and DNA traces[8].
3. Recovering complete tooth from solid matrices (acrylic) in which it is included is not always possible, since preserving the piece as evidence is not an objective of these techniques[9].
4. Teeth receive careless and aggressive handling from the moment they enter the laboratory for processing, causing many false positives and/or low yield of obtained DNA.
5. Current pulverization and endodontic access methods are limited only to obtaining gDNA for the determination of identity, but do not include the study and determination of cause of death and estimation of post mortem interval from the obtained dental pulp or gDNA. Besides, the destruction of the tooth prevents subsequent examinations and delivery of the piece as remains to relatives.

Use of DNA in Forensic Dentistry

In forensic and criminological identification there are situations in which the conditions of the body difficult the use of classical thanatological techniques[10] to obtain the macroscopic background of the body or the remains or they do not provide enough data to obtain satisfactory results. This is what happens for example in most major massive disasters such as plane crashes, shipwrecks, fires, explosions, or in situations where a corpse has been degraded because of the time it has been subjected to the environment[11, 12, 13].

In many of these situations the found remains are limited to a piece of maxillary or mandibular bone, or teeth that could contain valuable information when analyzing their genetic material.

Although it is possible to use any tissue containing cells as a source of DNA, not all of them are ideal for laboratory analyses, the quality of the DNA obtained, and its concentration and integrity can be affected by the aforementioned factors.

The oral cavity is a rich reservoir of cells and body fluids, as well as an area that gives a natural resistance to external physical changes, which otherwise easily destroy its component structures[14].

Use of Teeth as DNA Source

Teeth differ in shape and size but have a similar histological structure and cell rich tissues, specifically the dental pulp. The dental pulp is surrounded by a rigid wall cavity formed by the dentin. The dentin surrounds the pulp almost entirely, except at the tooth apex area, where it is communicated with periodontal tissues[15]. Within the dental tissues it can be found a large amount of cells suitable as a source of DNA, as odontoblasts, fibroblasts, undifferentiated mesenchymal cells, besides the white blood series, such as macrophages, lymphocytes and other, and cementocytes from root cement.

First studies in 1989 showed that it was possible to use the dental tissues as source of DNA. Yamada and Yamamoto[4] extracted DNA from pulp samples for forensic purposes, subjecting them to a study of restriction fragment length polymorphism (RLFP) and using radioactive probes for "MYO" human minisatellite. Their results indicated that it was possible to obtain DNA from pulp samples, and it was useful in identifying individuals, paternity test and gender determination. Other studies have also shown that the tooth and the pulp are an excellent source of high molecular weight DNA[16] and that in cases where samples are highly degraded, the tooth DNA is better preserved than DNA found in bones[14, 16].

Malaver and Younis[15] conducted a study in order to evaluate different dental tissues as DNA sources. They used 20 teeth obtained from unidentified bodies with 5 years. By sectioning the teeth with a high speed hand piece they obtained 20 samples of dentin and 20 samples of cement but they could obtain pulp samples only from 5 teeth. Their results indicated that the best quality of gDNA was obtained in cases in which it was possible to find the pulp for DNA, however, it was found only in 25% of the teeth after 5 years postmortem[15].

Teeth are widely used by archaeologists and anthropologists in determining characteristics of long term remains, whether mummified or in state of skeleton. Although the teeth contains a large amount of nucleated cells and that its high resistance to environment make them an excellent source of genetic information, they have the major disadvantage of requiring a lot of handling in the obtaining and processing of the sample, increasing the chances of contamination with foreign DNA. This is vital, especially in late post mortem interval, where the gDNA is scarce and difficult to obtain due to the high molecular degradation, therefore false results may be obtained by inclusion of DNA from the researcher[5].

Techniques for Obtaining DNA from Teeth

Early techniques for extracting pulp samples were performed using endodontic access by the use of pulp extractors, without a predetermined methodology[4, 6].

Carrasco et al.[7] obtained good results in teeth with fresh pulp, using endodontic files. With the passage of time, most of the pulp tissue is degraded to the point that the pulp extraction with endodontic instruments (hand files) becomes difficult[7]. The limitation of these methods is that organized pulp tissue is needed for endodontic instruments can operate more efficiently and this depends on the post mortem interval or time since tooth extraction. This is why much of the development of techniques have focused on obtaining both tooth tissues (hard and soft), for obtaining mitochondrial or gDNA. This determined the design of new methods, which included the complete pulverization of the tooth, as a way to ensure to obtain the trace DNA and cell debris present in the pulp and cement[17].

Smashing and Cold Pulverization

During 1993 Smith et al.[17] proposes the complete tooth pulverization using a hydraulic press, postulating that through this mechanism, there would be a greater quantity of DNA by the use of all available cells. Obviously the use of this technique involves the total destruction of the sample, and prevents its use for subsequent examinations. This method achieved yields of 18.1 ug of DNA per gram of tooth powder. It should be noted that the constant handling of these samples would mean that much of the DNA correspond to contaminants. During 1998, Sweet et al.[2] suggested the use of cryogenic semi automated mills for the pulverization of the teeth. This technique has replaced the technique of Smith, because the method is relatively simple and requires less handling of the sample, thus reducing the possibilities of contamination[2]. The main problem of this technique is the complete destruction of the sample, which prevents subsequent examination (estimation of post mortem interval and determination of cause of death), or delivering it to relatives.

Embedment of the Samples in Solid Matrices

In 2003, Gilbert et al.[5] established a new technique for archaeological studies of mitochondrial DNA in antique teeth, trying to control contamination. They included dental samples in liquid silicone and then waited for its polymerization. This would avoid any direct contact between the researcher and the tooth sample. For obtaining the sample of the dentin-pulp complex, they transversely cut the apex, and introduced a turbine through the dental root for obtaining a pulverization of the dentin-pulp complex. From 43 samples, only 4 showed evidence of contamination, but the mitochondrial DNA information could be obtained from all samples[5]. The latter approach involves endodontic and tooth section access, this method involves extensive handling that significantly increases the chances of contamination with foreign genomic and mitochondrial DNA[3]. The most important limitation of this method is that obtaining mitochondrial DNA is useful for archaeological studies (population genetics, migrations, etc.) but not for the determination of identity.

In 2007, Tran-Hung et al.[8] published a method with the objective of analyze the presence of specific microorganisms in the dental pulp for endodontic flora analysis. Modifying Gilbert technique[5] they designed a protocol that isolated the tooth from the external medium by including the sample in a resin. They did not use a turbine for the extraction of the material from the chamber and root canal. They introduced the different chemical reagents that destroy the cell membrane from the tissues and release the gDNA into the system, homogenizing the tissue without removing it from the pulp chamber[8]. This technique theoretically would obtain all of the cells of the pulp chamber, even if the tissue was found disintegrated, because the chamber and root canals act as a safe, keeping inside the disintegrated tissue as powder. In that study they used different recently extracted teeth, achieving easily the extraction of pulp DNA, with an average concentration of 228 µg per sample, making this method very useful for any type of genetic analyses. Despite this protocol was designed for the detection of microorganisms within the dental pulp, it could be used for genetic profiling of the donor, making it very useful in forensics. This study was related to "recently extracted" samples, that is, the possibility to find fresh and entire pulp tissue was very high, therefore the presence of cellular elements greatly facilitated obtaining gDNA. It should be noted that cases of late post mortem interval (over 1 year) are really tough cases, and the enzymatic digestion of pulp tissue prevents any later biochemical, cytological and histological examination.

Estimation of Post Mortem Interval

Estimating post mortem interval remains as one of the most complex unsolved problems in forensic pathology. The accuracy and applicability of the procedures depends on the characteristics and circumstances of death and postmortem interval. In the first 24 hours the combination of the study of vitreous humor potassium and rectal temperature gives acceptable results that improve with the incorporation of additional elements[18]. The publication of Henssge nomogram[19] has led to the introduction of the joint analysis of a number of variables that allow estimation of post mortem interval; however, reality continues demonstrating the need to improve the accuracy. The combined use of temperature and biochemical methods, improves the estimates provided it is done in the first 24 hours, after which the accuracy decreases in proportion to elapsed interval. Incorporating the spectrophotometric study of lividities and the study of entomofauna give new contributions for estimating post mortem interval, but like other methods, have disadvantages, especially after a certain time.

There are few references related to the estimation of post mortem interval through the use of teeth or tissues that compose them. Most of these studies focus on structural, biochemical, and morphological analyses of dentin-pulp complex in samples with early post mortem interval. In 2003 Boy et al.[20] used the degradation of pulp DNA in time as postmortem marker, determining that up to 144 hours after death the pulp DNA remains intact. In 2009 Vavpotic et al.[21] counted the number of odontoblasts present in the pulp related to the postmortem time and found that 5 days after death it is not possible to histologically visualize the presence of whole cells. Caballin et al.[22] in 2010 performed an assessment of the histological pulp changes for estimating post mortem interval, preliminary results show three stages in the gradual loss of pulp parenchyma and its organization until the seventh day after death. This method can only be used in estimating early post mortem intervals (in this case, less than one week).

Works related to functional, structural and molecular study of dental pulp in time, are bounded to early post mortem interval, wherein there are other accurate alternatives from the forensic point, the problem arises in late post mortem interval (more than 1 year since death).

Determination of Cause of Death

There are no studies showing post mortem analysis of dental pulp with forensic purposes, neither biochemical studies of pulp proteins nor their relationship with individual characteristics.

Therefore, the contribution that pulp tissue could deliver from a forensic toxicological point of view has been little studied, probably due to the difficulty in obtaining good quality pulp tissue and sufficient amount to allow the application of toxicological techniques for detecting traces of drugs, pesticides, heavy metals, etc.

Thus the biochemical and toxicological analyses of the dental pulp allows determining individual characteristics such as pathologies, diabetes, inflammatory state, etc. and/or determining possible causes of death of a victim.

Scientific evidence shows that the answer to forensic unknowns, are far from a resolved issue in forensic science.

The careless treatment is applied to dental tissues (pulverization, cut, friction producing heat, strong enzymatic action, etc.) is not understood since dental tissues deliver so valuable genetic information and further aspects that contribute to the estimation of post mortem interval and determination of causes of death can be studied from them.

STATE OF THE ART

Document of Ohira and Yamada[23] disclosed determination of a nucleotidic sequence of 452 bp of the D-loop region of mitochondrial DNA (mtDNA) from the amplification by PCR of samples extracted from 40 teeth. DNA was extracted separately from the pulp and the dentin of the same tooth. This work is only referred to mtDNA that is useful for studying antropology and genetic of populations, and not for determining identity.

Document of Malaver and Yunis[15] assessed different dental tissues as DNA source for forensic analysis. The pulp was obtained by cutting the teeth with a high speed hand piece, and dentin and cement were obtained by drilling with a high speed hand piece. This method use invasive and high-speed rotating tools that does not allow the preservation of the tooth.

Document of Tilotta et al.[24] compared obtaining of dental pulp by crushing the tooth and by removing pulp by standard endodontic access with trepanation of the occlusal surface. They did not propose any previous treatment of the tooth in order to obtain better results, nor morphological, cytological, histological, or toxicological analyses of the pulp for estimation of post mortem interval or cause of death.

Document of Pinchi et al.[25] disclosed the possibility of gDNA extraction by an endodontic technique. They used a diamond drill for introducing endodontic hand files in teeth for removing pulp remains in a first step, and then for introducing endodontic paper points for absorbing the residual pulp remains. They extracted gDNA with two commercial kits. After three months they repeated the procedure and were able to extract gDNA again, proving that the procedure was not effective in removing the whole pulp remains at the first time.

Document of Smith et al.[17] disclosed different techniques for obtaining dental DNA, such as, crushing the tooth, endodontic techniques and different cuts of the tooth. This document does not mention any previous treatment to the tooth nor morphological, cytological, histological or toxicological analyses of the pulp for estimation of post mortem interval or cause of death.

Previously, and up to the date of filing of this application, and up to the best of the knowledge of the inventors, there is no published report indicating a unique dental forensic method for obtaining genetic profiles, for estimating post mortem interval and for determining cause of death.

Definitions

The term "post mortem interval" or "post mortem intervals" as used in the present invention must be understood as the time between death and the discovery of the body or the analyses of the samples taken from the body. In case of examples, there are samples taken from donors alive, in that case, time since extraction of the tooth or exodoncy is the time that is considered as post mortem interval.

The term "early post mortem interval" as used in the present invention must be understood as the time between death and the discovery of the body or the analyses of the samples taken from the body, when less than 1 year since death have passed.

The term "late post mortem interval" as used in the present invention must be understood as the time between death and the discovery of the body or the analyses of the samples taken from the body, when more than 1 year since death have passed.

The terms "dental pulp content", and "pulp content" as used in the present invention must be interchangeably understood as the loose connective tissue located inside the pulp chamber in the center of the tooth comprising or not dentin remains.

BRIEF DESCRIPTION OF THE DRAWINGS

FIG. 11-C shows sectioned dentinal tubules transversely (H).

SUMMARY OF THE INVENTION

Figure 1:
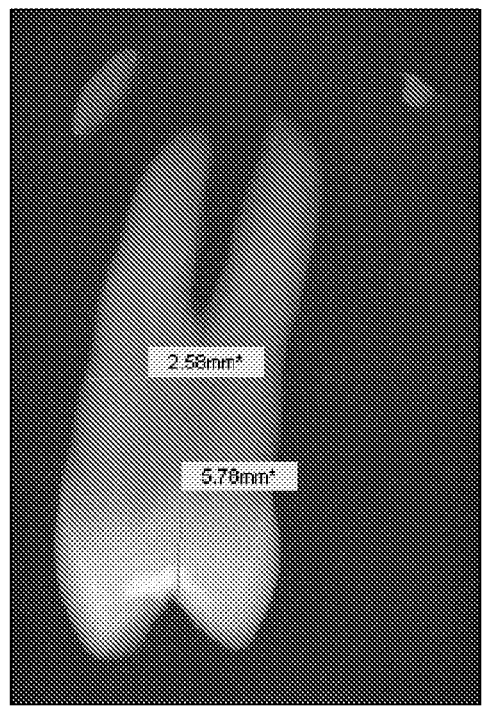
FIG. 1 shows an example of the measurement in (b) step of the method of the present invention, of the distance between the pulp chamber and the occlusal face or the palatine face, and between the radicular surface and the root canal at the level of the apical third.

The present invention is related to a method for determining or estimating the aforementioned forensic unknowns, developing and implementing a method that should be given to the tooth that is to be used in forensic dentistry allowing obtaining of gDNA from dental structures (pulp content, root cement) for forensic identification, estimation of post mortem interval (early and late) and determination of possible causes of death, these latter two are very little addressed by forensic dentistry.

gDNA is obtained from the samples of rehydrated dental pulp content and rehydrated root cement for determining genetic profile, gender, species, number of individuals, racial tendency, age determination and/or phenotypic profiles. The samples of rehydrated dental pulp content are also subjected to histological and cytological analyses through optical microscopy for estimating post mortem interval and to biochemical and toxicological analyses for determining possible causes of death.

The invention resolves the forensic unknowns of species, number of individuals, racial tendency, gender, age, genetic profile, phenotypic profile, post mortem interval and cause of death, overcoming the problems of the current techniques.

Unlike existing methods, discussed above, the present invention proposes an entirely different handling of the tooth and use of non invasive tools, as low-speed rotating tools, preserving the integrity of the tooth, then, it is possible to subject it to further analyses, to keep it as evidence or to deliver it to relatives as remains, allowing analysis of samples with early and late post mortem intervals, and preventing contamination of the samples.

This method involve the rehydration of the tooth for the reproduction of the physiological conditions, that is, external conditions of the tooth in the mouth and internal conditions of the tooth (pulp content and root cement) in the bone structure, obtaining root cement tissue for recovery of gDNA, and obtaining pulp tissue using an endodontic file in a low-speed rotating tool for gDNA extraction and for assessment of the morphology, cytology, and histology of the pulp content for estimating post mortem interval, and for biochemical and toxicological analyses of the pulp for determining possible causes of death and/or individual characteristics, such as, for example pathologies, from a single tooth.

DETAILED DESCRIPTION OF THE INVENTION

The present invention describes a new dental forensic method for obtaining dental pulp and useful gDNA from dental tissue (pulp content and root cement) for forensic identification (obtaining genetic profiles for determination of specie, number of individuals, racial tendency, gender, age (telomeres[1]), identity, phenotypic profile) and for estimation of post mortem interval and determination of possible causes of death, maintaining the integrity of the tooth for delivering to relatives or for further analyses.

The method of the present invention for forensic identification, estimation of post mortem interval and determination of possible causes of death comprises the steps of: (a) obtaining a tooth; (b) taking a digital radiography to the tooth; (c) external rehydrating of the tooth; (d) perforating the rehydrated tooth; (e) internal rehydrating of dentin pulp complex (f) obtaining rehydrated root cement; (g) obtaining rehydrated dental pulp content with a low speed rotation tool; and (h) storing, preservation, processing and/or analyses of the rehydrated dental pulp content and rehydrated root cement.

Tooth Source

The tooth obtained in (a) step can be a tooth from a dead body, a tooth from squeletal remains, a tooth found in a criminal scene, or any tooth to which it must be determined the identity of the person to it belonged.

Chronological Age and Evaluation of the Sample

There are biological evidences in individuals that can provide information for the identification of their chronological age. The biological factor corresponding to the translucent root dentine is directly related to chronological age of individuals. The translucency starts at the apex and extends gradually towards the cervical area of the root. It is possible to determine the age of an individual, through optical measurements of translucent root dentine. Tooth is placed under cold light and a picture is captured with a standard photo documentation system (5MP or more cameras). The system provides an image for qualitative analysis of translucency, using several data points for an accurate determination. The root translucency increases lineally with age, therefore, the age of the individual is determined using the standard chart for this technique[26].

In a preferred embodiment, previous to (b) step, age determination by translucent root dentine is performed.

The digital radiography of (b) step is taken to the tooth, previously cleaned and disinfected, with standard digital x-ray equipment and the image analysis is performed with any suitable software. The analysis of the digital radiography allows the definition of the distance between the pulp chamber and the occlusal face or the palatine face, and between the radicular surface and the root canal at the level of the apical third for determining and designing the best access or accesses (drilling) for (d) step. The analysis of the radiography allows also determining if the tooth is suitable to be used in this method. Teeth with root canal treatment, complete calcification in the pulp chamber and canals, pulpolites, apical lesions, abscess or fracture must be evaluated in order to determine if it is possible to use them for the method of the present invention.

The age determination at the time of death can also be determined by a study of the genetic material, determining the length of telomeres of gDNA obtained from dental pulp content or root cement as described below.

External Rehydrating Step (c) Step of external rehydrating of the tooth is performed immersing the tooth of (b) step previously cleaned and sterilized in external rehydration solution (ERS), for reproducing physiological conditions of the tooth when it was alive (relative humidity of 89% and 37° C.). In a preferred embodiment, the tooth is immersed in ERS during 24 to 120 hours at 37° C. In a more preferred embodiment, the tooth is immersed in ERS during 72 hours. The immersion of the tooth in ERS can be performed for example, but not limited to, in a plastic or glass tube or any clean container with a sufficient volume of ERS for enabling immersion of the tooth.

In one embodiment the external rehydration solution ERS comprises at least one polyol, and at least one mineral salt. The at least one polyol is selected for example among, but not limited to, glycerol. In a preferred embodiment the external rehydration solution ERS comprises distilled sterile water, sodium bicarbonate ($NaHCO_3$), sodium phosphate heptahydrate ($Na_2HPO_4$ $7H_2O$), potassium chloride (KCl), sodium chloride (NaCl), calcium chloride ($CaCl_2$), magnesium sulfate heptahydrate ($MgSO_4.7H_2O$), and glycerol. In a more preferred embodiment the external rehydration solution comprises: 1 L of distilled sterile water, 9 to 11 g of sodium bicarbonate ($NaHCO_3$), 6 to 8 g of sodium phosphate heptahydrate ($Na_2HPO_4$ $7H_2O$), 0.4 to 0.7 g of potassium chloride (KCL), 0.3 to 0.6 of g sodium chloride (NaCl), 0.02 to 0.06 g of calcium chloride ($CaCl_2$); 0.06 to 0.18 g of magnesium sulfate heptahydrate ($MgSO_4.7H_2O$), and 1 to 3% glycerol 100%, all in a solution buffered to ph=3.0 to 5.0.

Perforating Step (d) Step of perforating the rehydrated tooth is performed according to information of analysis of the distance to the pulp chamber and the root canals determined with the digital radiography of (b) step. This analysis defines the exact location and deep that the perforation(s) must have. One or more perforations can be made, for achieving the best rehydration in (e) step. Particularly, more than one perforation is performed when pulp chamber and root canals are tight. In a preferred embodiment a first perforation is performed from the occlusal face to the pulp chamber when premolars or molars are used and from the palatine face to the pulp chamber when incisors or canines are used (coronary permeability) and a second perforation is performed from the apical third of the root to the root canal (radicular permeability).

The perforation or perforations are performed with any precision tool that allows keeping integrity of the tooth and perforating it accurately and without generation of heat. In a preferred embodiment the perforation is performed with a portable dental unit and a high speed turbine with refrigeration. In a preferred embodiment, the perforation is performed with a 1 or 2 mm round diamond drill with air refrigeration. It must be emphasized that the perforation or perforations should be wide enough to allow entry of the internal rehydration solution (ISR) and a 2.5 mm file.

Internal Rehydrating Step (e) Step of internal rehydrating of dentin pulp complex is performed immersing the perforated tooth in internal rehydration solution (IRS). The IRS enters the pulp chamber and the canals through the perforation hole or holes performed in (d) step. The immersion of the tooth in IRS can be performed for example, but not limited to, in a plastic or glass tube or any clean sterile container with a sufficient volume of IRS for enabling immersion of the tooth. The IRS recreates the physiological conditions that the dental pulp had when it was alive (pH=7.4; 37° C.). In a preferred embodiment the rehydration of the pulp is performed during 24 to 96 hours. In a more preferred embodiment the rehydration of the pulp is performed during 72 hours. The step of rehydration is performed preferably in an incubator at 37° C. and 5% $CO_2$.

The internal rehydration solution is a standard cell culture media for human's cells without supplement of proteins and antibiotics. In a preferred embodiment, the internal rehydration solution (IRS) comprises mineral salts, sugars and polysaccharides, amino acids, vitamins, and nucleosides, all dissolved in a solution with an indicator of pH change (phenol red), and buffered for maintaining pH between 7.0 and 7.2. In a preferred embodiment the internal rehydration solution IRS comprises inorganic salts of calcium, magnesium, potassium and sodium in a concentration between 0.05 and 0.6 g/L, NaCl in a concentration between 6 and 7.5 g/L, glucose in a concentration between 0.8 and 1.5 g/L and hyaluronic acid in a concentration between 2 and 5 g/L, glutamine in a concentration between 0.2 and 0.35 g/L, other amino acids in concentrations between 0.01 and 0.03 g/L, vitamins (L-ascorbic acid, D-biotin, coline chloride, folic acid, among others) in concentrations from 0.0001 to 0.005, nucleosides (adenosine, cytidine, 2'-deoxyadenosine, among others) in concentrations between 0.005 and 0.015 g/L.

Obtaining Root Cement

The rehydrated root cement is obtained in (f) step using a blade for obtaining slices of root cement. In a preferred embodiment, the slices of root cement are from the apical third. In a preferred embodiment, an No 15 scalpel blade is used for obtaining the slices of root cement. Alternatively, another kind of instrument could be used (such as curette No 13/14), where soft tissue remains attached to the root surface.

Obtaining Dental Pulp

For obtaining rehydrated dental pulp content with a low speed rotation tool on (g) step a previous permeation of the chamber and the canals can be made with an endodontic hand file. In a preferred embodiment a K No 25 endodontic file is used for the previous permeation of the chamber and canals. (g) Step of obtaining rehydrated dental pulp content with a low speed rotation tool is performed with a file mounted on a low speed vertical-vibrating contra-angle endodontic hand piece. These kinds of instruments are normally used for root canal treatment and are specially designed for removing the complete dental pulp. The inventors realized that these kinds of tools are also useful for recovering the pulp and not only for removing it. In a preferred embodiment, the amplitude of the vibration is around 0.4 mm and the oscillations are between 3000 and 5000 oscillations per minute. After using the file mounted on the low-speed endodontic hand piece, the file is washed with sterile distilled water for recovering the pulp content, and the tooth is placed with the crown upside down in a centrifuge tube and is centrifuged at 3000 rpm during 3 to 8 minutes at room temperature for recovering the rest of the pulp content.

Final Processing of the Dental Pulp Content and Root Cement

In (h) step of storing, preservation, processing and/or analyses of the rehydrated dental pulp content and rehydrated root cement, the samples (of rehydrated dental pulp content and rehydrated root cement) can be directly processed and used for analyses or can be stored and preserved for performing the analyses later.

In one embodiment the samples of rehydrated dental pulp content and rehydrated root cement are stored at −80° C. and the processing and analyses are performed later.

In another embodiment the samples of rehydrated dental pulp content and rehydrated root cement are processed for obtaining gDNA.

gDNA can be obtained from rehydrated dental pulp content and rehydrated root cement through any suitable molecular biology technique. In one embodiment the gDNA is obtained through the use of magnetic beads for soft tissue (dental pulp content) and for hard tissue (root cement).

Absorbance at 260 nm and 280 nm is measured in a spectrophotometer for analyzing integrity, purity, concentration and presence of contamination.

Different analyses can be performed to the gDNA depending on the information the user needs to know:

For genetic profile determination: genetic profiles are obtained through gDNA analyzed by Multiplex PCR for 16 or 21 markers or Short Tanden Repeat (STR). The fragments are sequenced for obtaining an electropherogram (graph showing the size in base pairs (bp), the name of the STR and the allele of the individual for each peak).

For gender determination: analysis of expression of fragments corresponding to gene of amelogenine is performed. The analysis can be performed through a conventional PCR reaction using the proper primers. In a preferred embodiment, the genetic profile analysis through a Multiplex PCR for 16 markers or short tandem repeat (STR), and later sequencing of the gDNA fragment are performed. For amelogenine gene, one peak is observed for female gender and two peaks, corresponding to chromosomes X and Y are observed for masculine gender.

For species determination: all the genes involved in the present analysis of genetic profile are human genes, there is no cross reaction with other species, then, if valid results are obtained for the other analysis, the human species is confirmed.

For determination of number of individuals: if more than one peak is obtained in the analysis of the genetic profile for one STR (except for amilogenine gene), the sample correspond to more than one individual. Genetic profiles are unique and unrepeatable for each individual.

Racial tendency, age determination and phenotypic profiles are determined through genetic analysis of gDNA. For example:

For racial tendency determination: one of the most recent analyses of the DNA study allows determination of the geographical origin of the subject under study. Genetic information from the Y chromosome has very low rate variability with mutations every 357 generations[27]. It has been determined that there is a geographical distribution of Y chromosome caused by migration patterns and isolation of human beings, which would cause a specific variation of these patterns by region of origin of the individual. For this reason, using a Y-STR analysis it is possible to infer the origin of an individual[28]. This information could be useful in cases where it is unclear ethnicity of a body. There is an extensive database of halotypes of the STR-Y in Internet (http://www.yhrd.org) that can be used to infer the likely ethnicity of an individual or their ancestors[29].

For age determination: the age of an individual at the time of death, besides to the analysis of the digital radiography of the tooth, can also be determined by a study of the genetic material, determining the length of telomeres of gDNA obtained from dental pulp content or root cement[30]. Telomeres are structures that are located at the ends of chromosomes and are equal to 6 bp repetitive sequences (TTAGGG). These sequences are replicated at each cell division by telomerase, but imperfectly, since it does not replicate the last sequence of 6 bp so that telomeres are shortened as far as the individual ages, being a direct indication of the age.

For phenotypic profile (i.e., individual characteristics, such as height, eye, skin, and/or hair color, build, etc): There have been identified and analyzed genes that confer color to the hair[31, 32], and genes associated with the coloration of the iris[33, 34] making possible the identification of these characteristics by analysis of the gDNA of the individual.

Further analyses of the samples (rehydrated dental pulp content and rehydrated root cement) and the tooth can be performed depending on the information the user needs to know:

For estimation of post mortem interval: histological and cytological analyses through optical microscopy of the rehydrated dental pulp content, showing morphological transformations of the tissue in relation to the time passed since exodoncy (tooth extraction) or death are performed. Histological and cytological analyses are performed according to standard techniques. In a preferred embodiment hematoxylin and eosin staining (H&E stain or HE stain) is used for histological analysis. In another preferred embodiment Masson's trichrome staining is used for histological analysis. The present invention comprises a synoptic chart (morphological pattern versus time) that enables comparing the morphology (results of histological and cytological analyses) of a sample in any forensic laboratory with histological and cytological analyses of standard samples with defined time since death showing the transformations at different times. The analysis of morphological changes of each sample enables its classification in four different levels for the characteristics observed in the samples from the histological and cytological analyses: presence or absence of cell nucleus, blood vessels, lymphatic vessels, calcifications, density of fibroblasts and collagen fibers, and cell viability. These classifications allow the comparison of the samples with synoptic charts developed in the present invention indicating the changes observed with the time passes since dead, allowing therefore the estimation of early post mortem interval (less than 1 year), and late post mortem interval (more than 1 year), at least until 40 years of post mortem interval.

For determination of possible causes of death and individual characteristics: biochemical and toxicological analyses of the rehydrated dental pulp content are performed. These analyses enable the determination of possible causes of death, such as, for example, but not limited to, presence of pesticides, chemical elements, heavy metals, poisons, drugs, drug abuse, possibly causing the death or pharmacological information on aspects related to systemic conditions of the victim, such as treatments with drugs for determined individual characteristics, such as, pathologies possibly causing the death (diabetes, hypertension, cancer, etc).

Further analyses of the tooth, keeping it as evidence or delivering it to relatives as remains is possible due to the tooth maintains its integrity after the method of the present invention.

The method of the present invention enables obtaining gDNA from dental pulp and root cement from teeth with early and late post mortem interval with less manipulation and more integrity of the gDNA, due to the double rehydration of the tissues and the use of low speed tools that produce less heat and keep the samples in better condition. The method that also allows recovery of complete dental pulp content, as a pure structure, enables evaluation of morphological, histological and cytological changes of the pulp content in time, for estimation of post mortem interval. The rehydrated dental pulp content can also be subject to biochemical and toxicological analyses, for determining possible causes of death. The method also allows keeping the complete tooth as evidence for further forensic analysis[35], as evidence, and for being delivered to relatives.

The present invention add value to the tooth and pulp content, since other researchers in their attempt to obtain gDNA have treated the tooth and its content in a very aggressive manner (pulverizing, cutting with discs, with strong enzymatic action, etc.). There is no evidence in the literature that presents a comprehensive and conservative point of view of the tooth. This method improves the existing designs incorporating an increase in the value of the tooth and the pulp content in the sense of preventing the destruction of tooth or immobilization in acrylic matrices, which also hinders its full recovery. The new method provides the best conditions to tooth structure and content to enable a full recovery of pulp content and gDNA. This is achieved by protecting the tooth and its pulp content, recreating the conditions in which they were in life, that is, with high humidity outside, at 37° C. and with humidity inside of the pulp chamber.

New analysis are possible with the new method, that were impossible until now: optical microscopy analysis of the pulp content, which shows the morphological, histological and cytological changes of the pulp content in time, pulp content toxicological analysis for determining possible causes of death and biochemical analysis of the pulp content for determining individual characteristics, such as for example, pathologies.

This method allows making a synoptic chart of morphological pulp markers that change in time, which can be applied in estimating post mortem interval. Portions of the pulp content obtained from the same tooth or from other tooth are used for toxicological and biochemical analyses that allow the determination of individual characteristics (pathologies) or the possible cause of death, besides obtaining gDNA to determine genetic and phenotypic profile to give response to the unknowns aforementioned. It also preserves the integrity of the tooth.

The use of low-speed rotary instruments for removing pulp content is an important part of the present invention because they produce less heat and damage than high speed tools which are commonly used in other methods. Low-speed rotary instruments used in the present invention (usually used in root canal treatments) are specifically designed for the complete removal of the dental pulp or its remains, allowing morphological analyses, which were totally impossible until now.

The present invention is useful for forensic identification process, determination of cause of death, and estimation of post mortem interval (early, and late), among other analysis.

Any kind of teeth can be used for the method of the present invention, comprising permanent or deciduous teeth, unirradicular, birradicular or multirradicular teeth, incisors, canines, premolars or molars, belonging to persons with any age and gender.

Kit Components

The present invention also provides a kit for forensic identification, estimation of post mortem interval (early and late) and determination of possible causes of death, comprised by the following elements:

1.—Propilene sterile tube for the sample.
2.—Propilene sterile tube with the ERS solution.
3.—Petri dish 10 mm
4.—Scalpel Blade No 15.
5.—Eppendorf tube.
6.—Round diamond drill (2 mm)
7.—Endodontic hand file K, No 25.
8.—Propilene sterile tube with the IRS solution.
9.—Petri dish 10 mm
10.—Endodontic hand file K, No 30.
11.—File of SAF system 2.5 mm
12.—Falcon sterile tube 15 ml.

INDUSTRIAL APPLICABILITY

The present invention is applicable in analyses and researches of forensics and criminalistics for determining identity and cause of death and for estimating post mortem interval of victims or persons involved in judicial or criminal incidents, such as, for example, but not limited to natural disasters (earthquakes, tsunamis, fires, etc), massive disasters (natural, terrorism, aviation, sea or land accidents, war, etc), and natural death, accidental death or death caused by third parties. The present invention is useful for estimating post mortem interval for early and late post mortem intervals.

EXAMPLES

Example 1 gDNA and Genetic Profiles Obtained with the Method of the Present Invention 1.1. (a) Teeth Obtaining
1.1.1. Inclusion Criteria:
11 permanent human teeth, unirradicular or birradicular (molars, premolars, and incisors), numerated from 1 to 11. Table 1 shows the characteristics of the samples.

Gender, age, time since extraction or post mortem interval and individual characteristics of the donors previously known in order to confirm the results of the method. Teeth with intact structures.

TABLE 1

Characteristics of the samples.

| Sample code | Name of tooth (International nomenclature) | Time since extraction | Gender [F or M] | Age of the human [years] |
|---|---|---|---|---|
| 1 | Right maxillary first premolar (1.4) | 38 years | M | 18 |
| 2 | Right maxillary first premolar (1.4) | 18 years 1 months | M | 48 |
| 3 | Left mandibular lateral incisor (3.2) | 1 year 3 months | M | 43 |
| 4 | Left mandibular central incisor (3.1) | 1 year 3 months | M | 43 |
| 5 | Left mandibular first premolar (3.4) | 2 weeks | M | 25 |
| 6 | Right mandibular third molar (4.8) | 3 months | M | 20 |
| 7 | Right mandibular first premolar (4.4) | 3 months | M | 25 |
| 8 | Left mandibular first molar (3.6) | 1 year 3 months | M | 60 |
| 9 | Right mandibular second premolar (4.5) | 19 years | M | — |
| 10 | Right mandibular first premolar (4.4) | 19 years | M | — |
| 11 | Right maxillary second premolar (1.5) | 22 years | M | 22 |

— not obtained 1.1.2. Exclusion Criteria:

Non vital teeth, teeth with root canal treatment, apical lesions, abscess, fracture or sectioned during exodontia were not considered for the method of the present invention.

1.2. (b) Taking a Digital Radiography to the Tooth.

A Digital Radiography was Taken to Every Tooth with an X Ray Equipment (Sirona, Heliodent, Charlotte, N.C. 28273, USA).

The distance between the pulp chamber and the occlusal face or the palatine face, and between the radicular surface and the root canal at the level of the apical third was measured with the software SIDEXIS (Sirona). FIG. 1 shows an example of this measurement.

Images were saved and the distances were registered in a worksheet for their further use in (d) step of perforating the rehydrated tooth for the access to the camber and the root canal.

The dental surface was decontaminated by successive washes in a buffered solution of salts at pH 7.0. Then the teeth were incubated during 10 minutes under germicidal UV light in a vertical flow hood (Zhicheng, Zhjh-c1106c cleanbench, Shangai, China), leaving the teeth in separate sterile tubes of 5 ml volume (Edlab).

1.3. (c) External Rehydrating of the Tooth.

4 ml of external rehydration solution (ERS) of example 1 were added to each sterile tube containing each tooth. The tubes with the teeth were incubated during 72 hrs in and orbital incubator (Mrc™) at 37° C.

The teeth were extracted from the tubes in a vertical flow hood (Zhicheng, Zhjh-c1106c clean bench, Shangai, China) after the incubation, and they were dried with sterile gauze.

1.4. (d) Perforating the Rehydrated Tooth.

A high speed turbine (Machtig) connected to a portable dental unit with air refrigeration (Dynamic Dynair) with new round diamond drills of 1 and 2 mm of diameter were used in the vertical flow hood for perforating the teeth according to the distances measured in (b) step.

A first perforation was performed from the occlusal face to the pulp chamber when premolars or molars were used and from the palatine face to the pulp chamber when incisors or canines were used (coronary permeability). The perforation was wide enough to allow entry of the internal rehydration solution (IRS) and a 2.5 mm file.

A second perforation was performed from the apical third of the root to the root canal (radicular permeability).

For both perforations abundant airflow was used for reducing heat generation.

Figure 2:
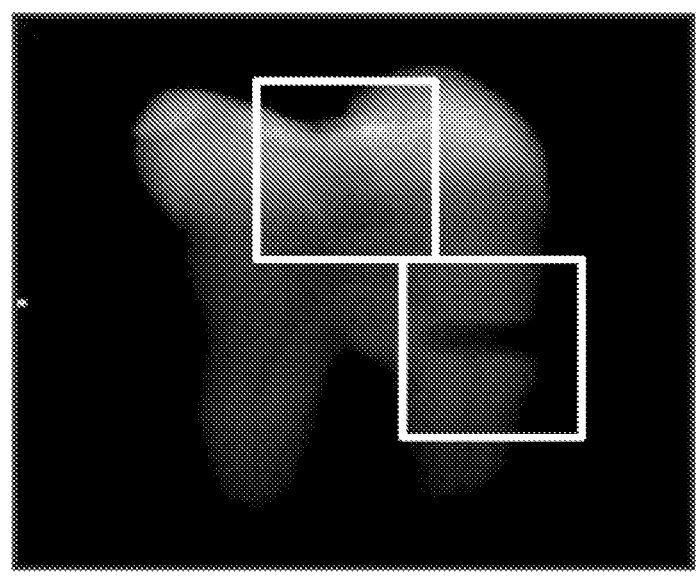
FIG. 2 shows and example of two perforations performed in (d) step of the method of the present invention, from the occlusal face to the pulp chamber (coronary permeability) and from the apical third of the root to the root canal (radicular permeability).

FIG. 2 shows an example of both perforations.

1.5. (e) Internal Rehydrating of Dentin Pulp Complex.

Perforated teeth were placed in separate sterile tubes of 5 ml volume (Edlab) containing 5 ml of internal rehydration solution (IRS). The tubes with the teeth were incubating during 72 hrs in an incubator at 37° C. and 5% $CO_2$ for rehydrating the internal structure of the dentin pulp complex.

The teeth were extracted from the tubes in a vertical flow hood (Zhicheng, Zhjh-c1106c clean bench, Shangai, China) after the incubation, and they were dried with sterile gauze.

1.6. (f) Obtaining Rehydrated Root Cement.

An No 15 scalpel blade mounted on a handle was used in a vertical flow hood (Zhicheng, Zhjh-c1106c clean bench, Shangai, China) for obtaining slices of root cement from the apical third.

1.7. (g) Obtaining Rehydrated Dental Pulp Content with a Low Speed Rotation Tool.

A previous permeation of the chamber and the whole long of the canals was made with a K No 25 hand endodontic file 4 to 5 times (radicular permeability). The K No 25 hand endodontic file was placed in a sterile Petri plate for recovering the possible pulp content and was washed carefully with sterile water.

SAF System (ReDent Nova, Israel) was used for obtaining rehydrated dental pulp content. SAF System is a hollow file in a low speed rotation tool designed for last step of root canal treatment for removing complete sick dental pulp or its remains.

The method of the present invention used SAF System for an alternative objective. Since the method, from a forensic point of view, needs recovering the higher content of pulp for obtaining free gDNA, cell nucleus, etc., this instrument is particularly useful.

The design of the file is very sophisticated, comprising an abrasive net that retains the pulp content inside it and at the same time it loses the pulp content retained in the walls of the pulp chamber. As the abrasive net acts as a fishing net it retains the content without damaging the remains of pulp, which is the objective of the method of the present invention, for obtaining useful gDNA and pulp content in good conditions for estimating post mortem interval and for determining cause of death.

A file of 2.5 mm was used in the SAF System with 4 to 5 back and forward movements. The aforementioned enabled loosing and removing the rehydrated pulp content that is released into the canal and removing the rehydrated pulp attached to the walls.

The file of the SAF System was placed in a sterile Petri plate for recovering the attached pulp content. The teeth were placed with the crown upside down in separate centrifuge tubes of 1.5 ml and they were centrifuged at 5,000 rpm (Labnet International, PrismR, USA) during 5 minutes at room temperature.

A precipitate with the pulp content was obtained (cells, free gDNA, fibrous tissue and dentinal remains). The teeth are removed from the tubes and saved as evidence or for further analysis.

1.8. (h) Storing, Preservation, Processing and/or Analyses of the Rehydrated Dental Pulp Content and Rehydrated Root Cement.

The sample of pulp content was separated in three parts: one for obtaining gDNA (genetic profile, gender determination, specie determination, determination of number of individuals, racial tendency determination, age determination through telomeres, phenotypic profile); one for morphologic analysis (histological and cytological analyses for estimation of post mortem interval) and one for biochemical and toxicological analyses (for determination of possible causes of death and individual characteristics).

The samples of pulp content and slices of root cement were placed in separate tubes and were storage in a Thermo Scientific 700 Series freezer at −80° C. for their further processing.

1.8.1. Obtaining of gDNA from Pulp Content and Root Cement.

One of each samples of rehydrated pulp content and the samples of slices of rehydrated root cement were thaw for obtaining gDNA.

The extraction of gDNA was performed through an automatic system for purification of nucleic acids by the use of magnetic particles with a minimum volume of sample (Maxwell 16 Promega® Co-USA AS2000). A demineralization pretreatment before the gDNA extraction was performed in the case of samples of root cement samples.

A thermo cycler (Applied Biosystems, 7.500 Real time PCR System, California, USA) was used for quantifying gDNA and analyzing integrity, purity, concentration and contamination. This equipment enabled quantification by real time PCT using Quantifiler® DUO kit for the genetic products in Table 2.

TABLE 2

Quantifiler ® DUO kit targets

| Target | Gene target | Location | Amplicon length bases | Gene ID | Ploidy |
| --- | --- | --- | --- | --- | --- |
| Human target | Ribonuclease P RNA component H1 (RPPH1) | 14q11.2 | 140 | 85495 | Diploid |
| Human male target | Sex-determining region Y (SRY) | Yp11.3 | 130 | 6736 | Haploid |

After quantification, a Multiplex OCR for 16 markers or STR (Short Tanden Repeat) was performed, and the DNA fragments were sequenced in a sequencer (Applied Biosystems, 3130 Genetic Analyzer, California, USA). The sequenced fragments were represented in standardized charts (electropherograms) for determining the alleles for 15 autosomic STR markers and for the gender of the individual using the Applied Biosystems Identifiler™ Plus kit. Also it was used The PowerPlex® 21 System (Promega) for STR analysis of human forensic samples, amplification of all 13 CODIS loci: D3S1358, D5S818, D7S820, D8S1179, D13S317, D16S539, D18S51, D21S11, CSF1PO, FGA, TH01, TPDX and vWA, plus Amelogenin, Penta D, Penta E, D1S1656, D2S1338, D6S1043, D12S391 and D19S433.

gDNA and Genetic Profile Results.

Figure 3:
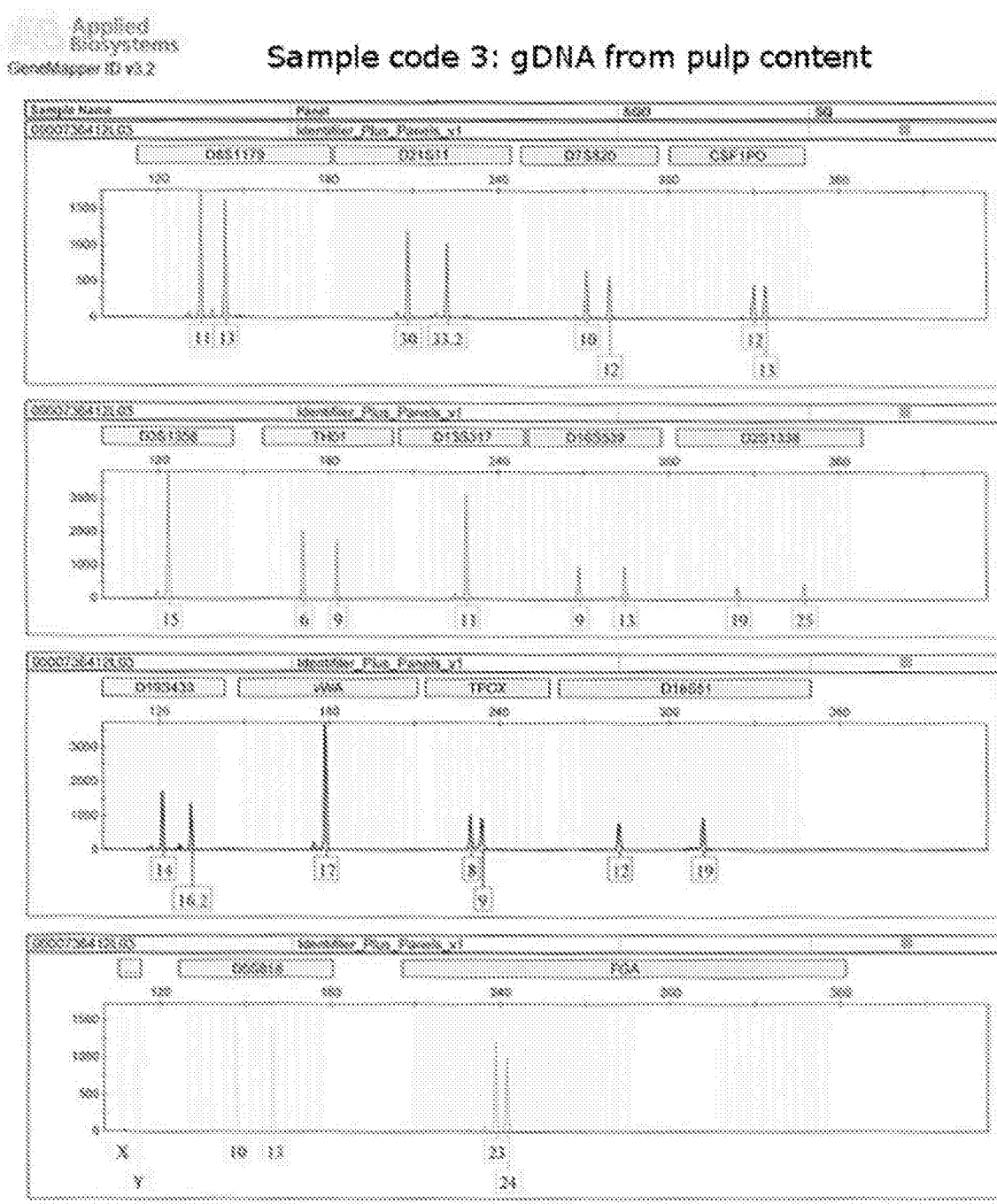
FIG. 3 shows the electropherogram of sample code 3 of Example 1 for gDNA obtained from pulp content.
Figure 4:
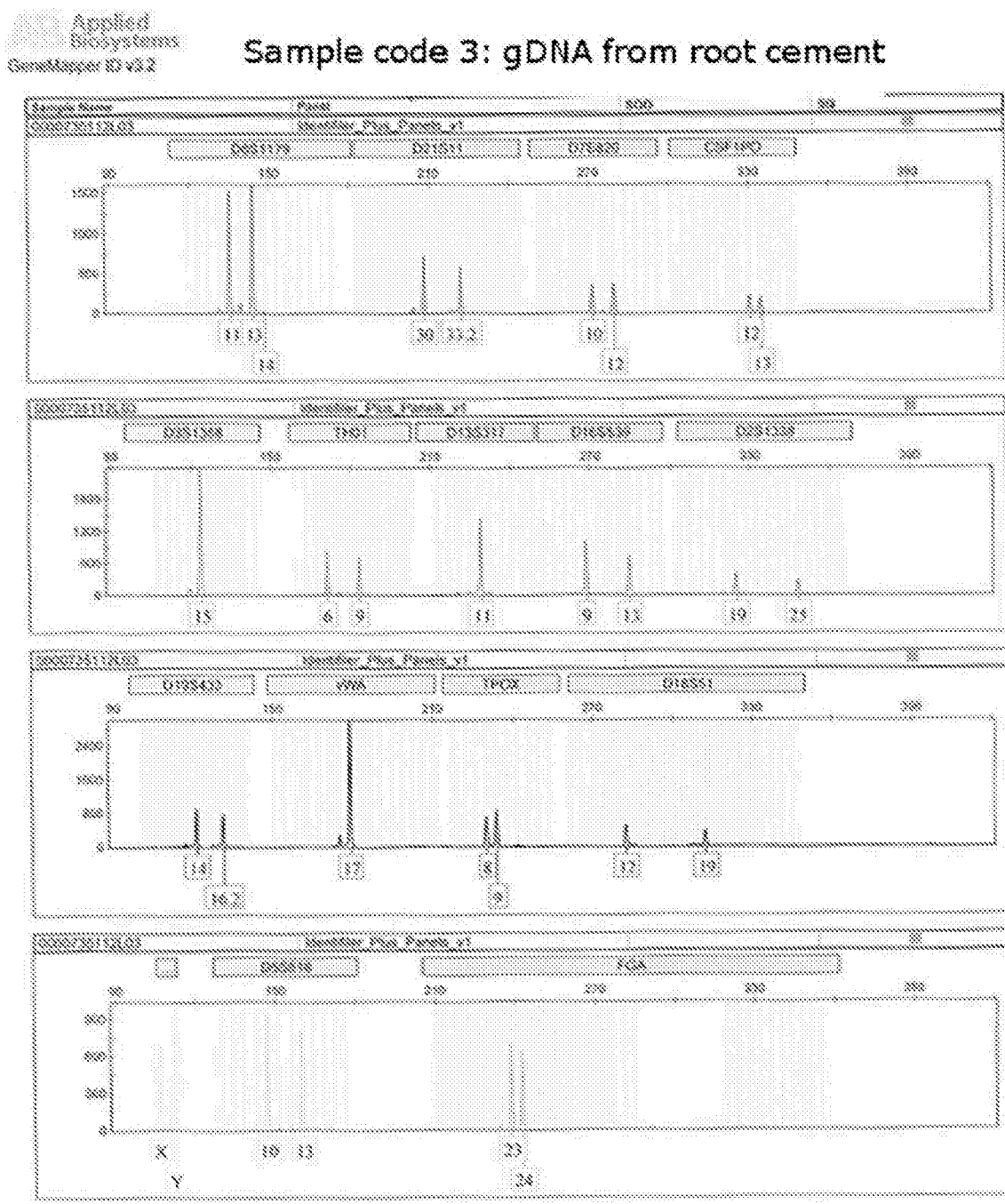
FIG. 4 shows the electropherogram of sample code 3 of Example 1 for gDNA obtained from root cement.

The best result was obtained with sample code 3 and 4 (Table 3) corresponding to a time since extraction of 1 year and 3 months. In this sample it was possible to obtain a complete genetic profile from the gDNA extracted from the pulp content (FIG. 3) and from the root cement (FIG. 4). FIGS. 3 and 4 show identical genetic profiles, gender and human specie are ratified.

Figure 5:
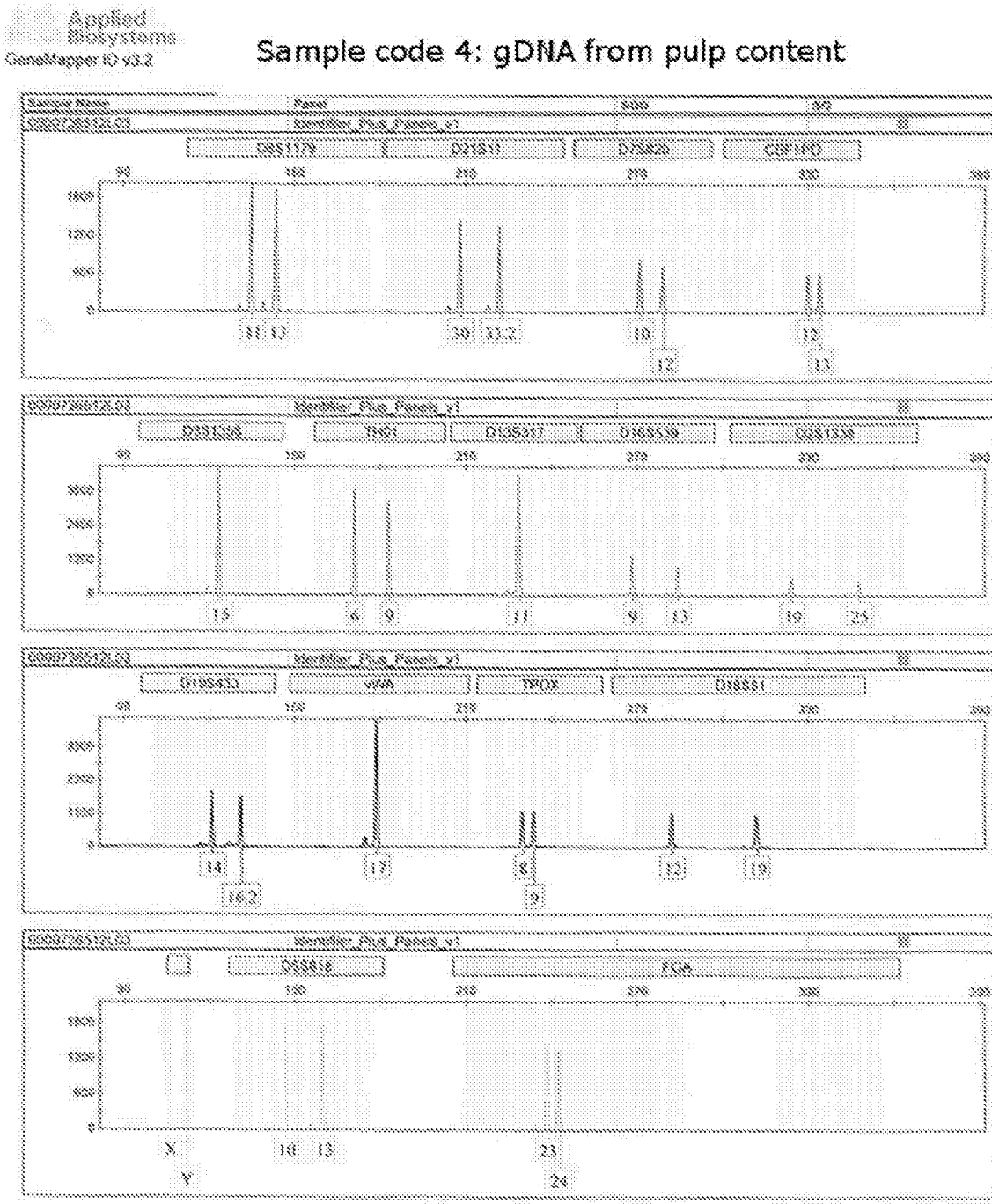
FIG. 5 shows the electropherogram of sample code 4 of Example 1 for gDNA obtained from pulp content.
Figure 6:
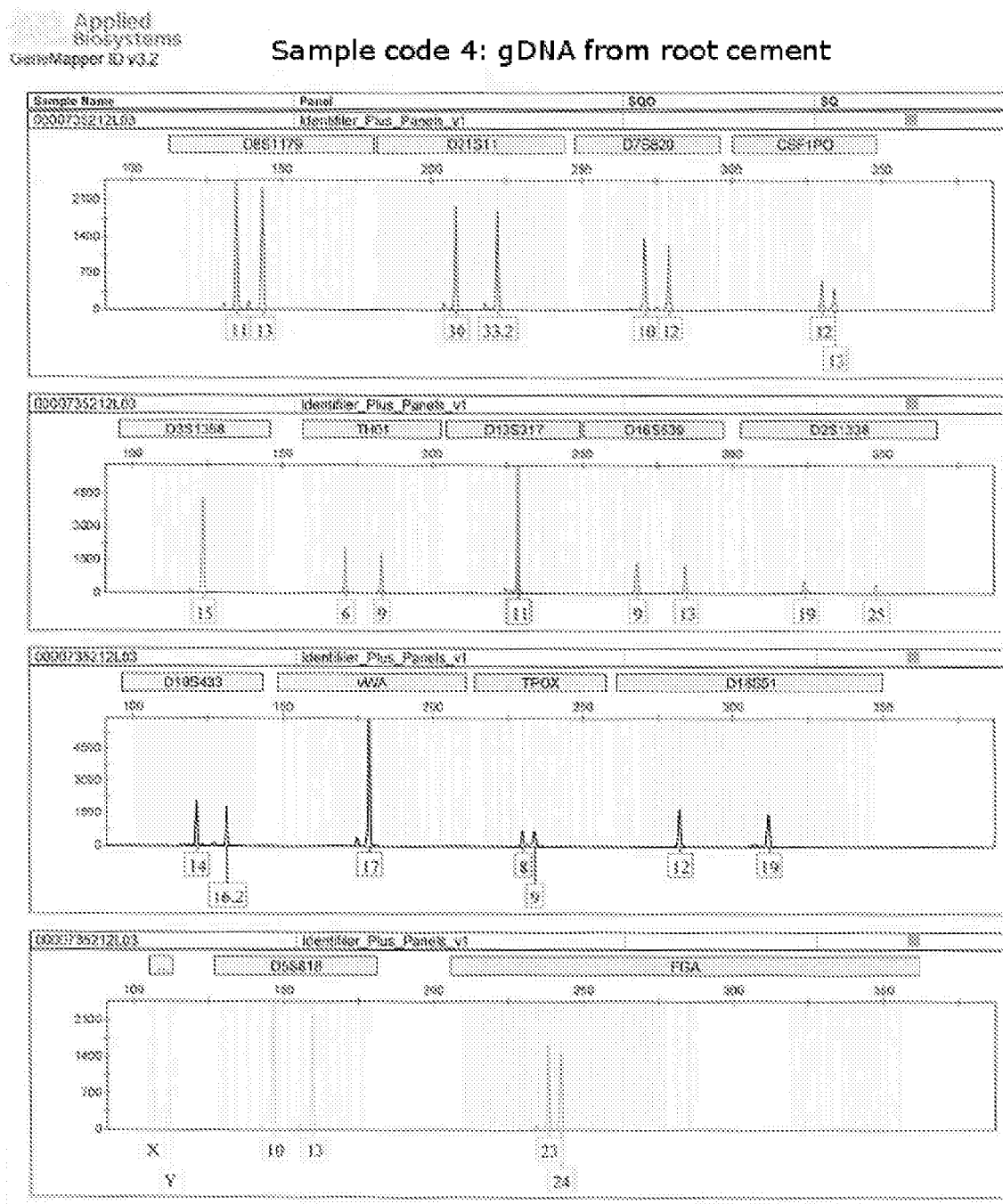
FIG. 6 shows the electropherogram of sample code 4 of Example 1 for gDNA obtained from root cement.

Sample code 3 and sample code 4 (Table 3) are teeth of the same individual with a time since extraction of 1 year and 3 months. The electropherograms of this sample shows identical genetic profiles and gender for pulp cement (FIG. 5) and for root content (FIG. 6).

Figure 7:
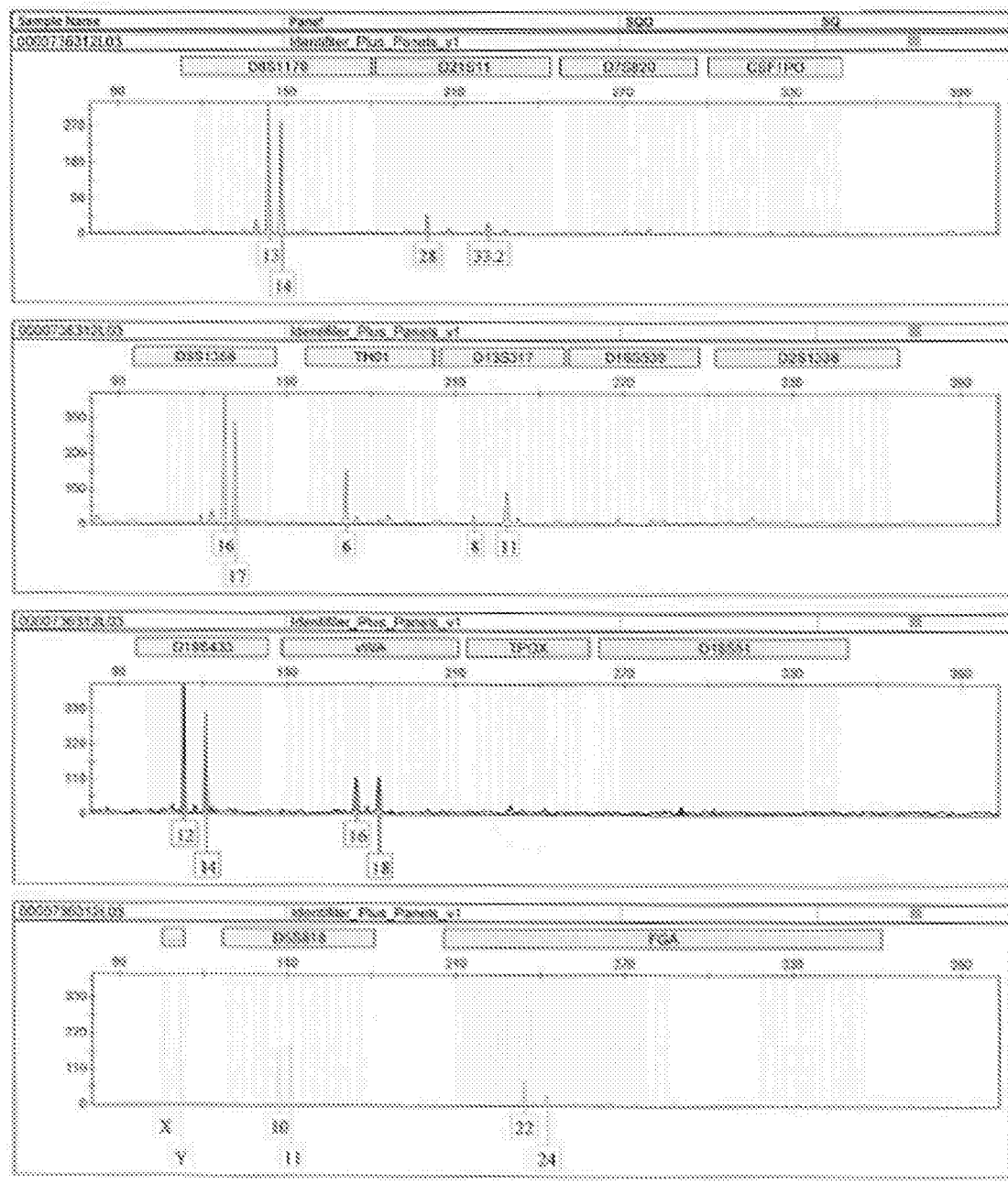
FIG. 7 shows the electropherogram of sample code 2 of Example 1 for gDNA obtained from pulp content.

FIG. 7 corresponded to the genetic profile obtained from the pulp content of sample code 2, this sample with a time of 18 years and 1 month since extraction. The autosomic genes were observed and the genetic profile was determined with Applied Biosystems Identifiler™ Plus kit and Power-Plex® 21 System (Promega).

Figure 8:
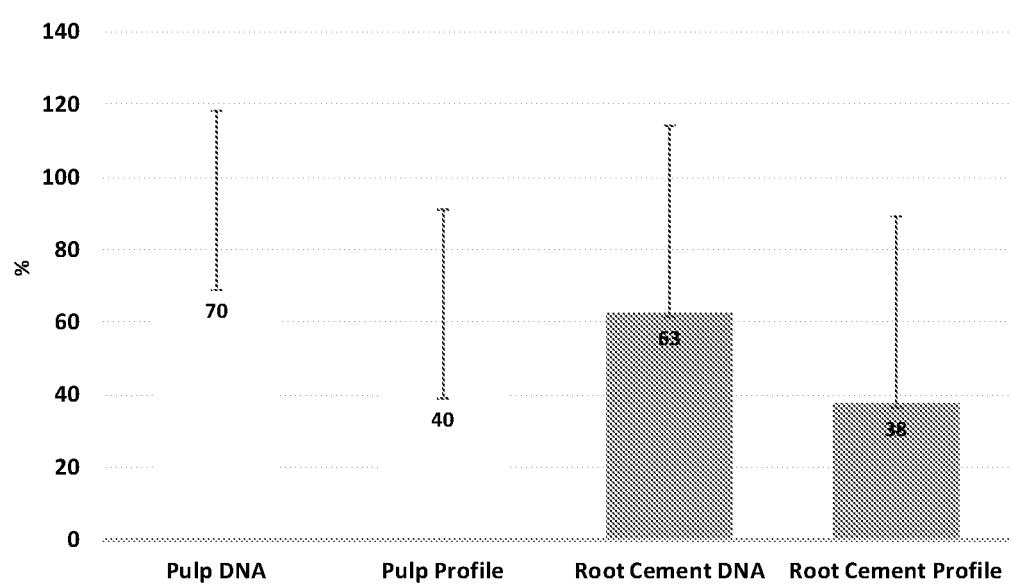
FIG. 8 shows the percentage of success in obtaining DNAg pulp and root content of 11 samples and the success rate in obtaining genetic profiles obtained from DNAg.
Figure 9:
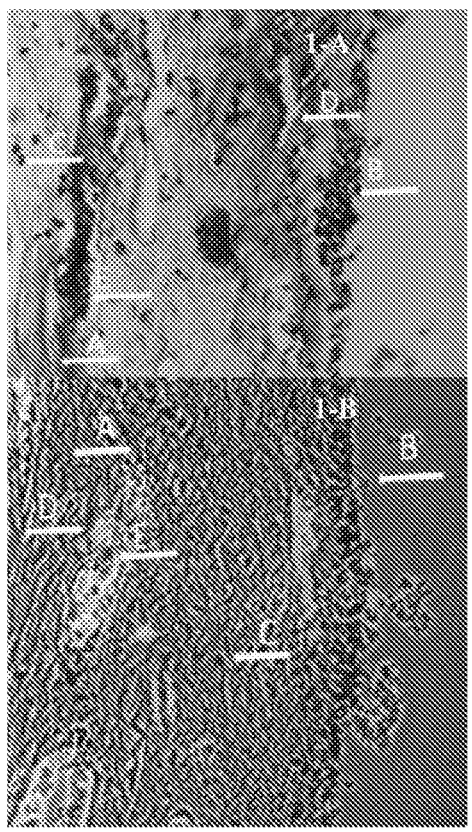
FIG. 9 shows fresh dental pulp (less than 24 h since extraction). Panel 9 (1-A) with hematoxylin eosin staining shows a connective like tissue, with abundant collagens fibers (A), in the periphery it shows nucleus in the odontoblast palisade (B) embedded in the collagen fibroblast nuclei are observed (C), nucleus are hyper chromatic stain, also are blood capillaries with loss indemnity in wall (D), inside red blood cells that lost their spherical shape (E). Panel 9 (1-B) shows a large network of collagen fibers (A) inside which hyper chromatic nucleus (C), blood capillaries with loss indemnity in wall (D) inside are observed capillary blood with loss of their characteristic spherical shape (E), on the right side of the image it shows a palisade of odontoblasts nucleus of hyper chromatic cores with altered form (B).
Figure 10:
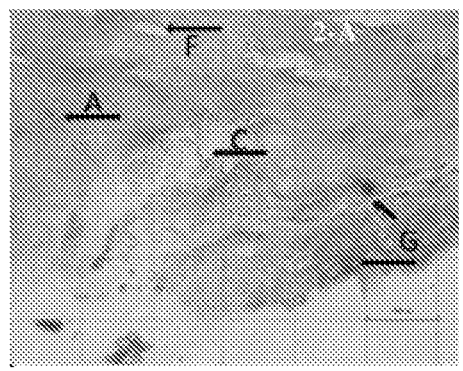
FIG. 10 shows dental pulp with one month since extraction. Panel 10 (2-A) shows a form loss of the classical pulp morphology, with abundant presence of fibrous tissue (A) with different thickness and empty areas (F). In the periphery of the sample, hyper chromatic area shown that could be to cell nuclei (G). No blood capillaries or red blood cells are shown and some undamaged cell groups are distributed in the sample. Panel 10 (2-B) and 10 (2-C) with collagen specific stain shows a sa large amount of blue collagen fibers (A), cellular groups are dispersed and retained their shape (C) (F) empty areas are observed. Towards the periphery hyper chromatic areas (cores) (G), and not observed red blood cells and capillaries blood.
Figure 10:
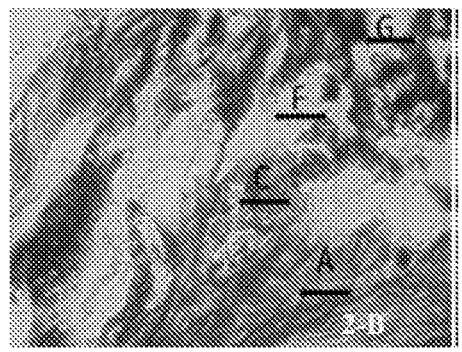
Figure 10:
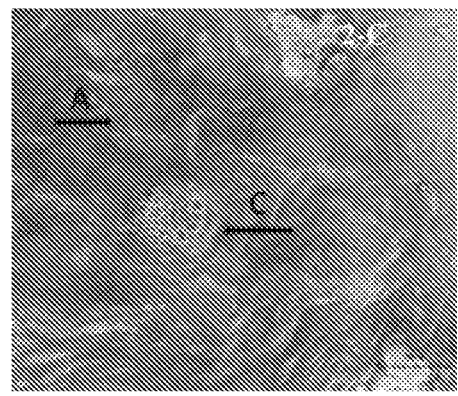
Figure 11:
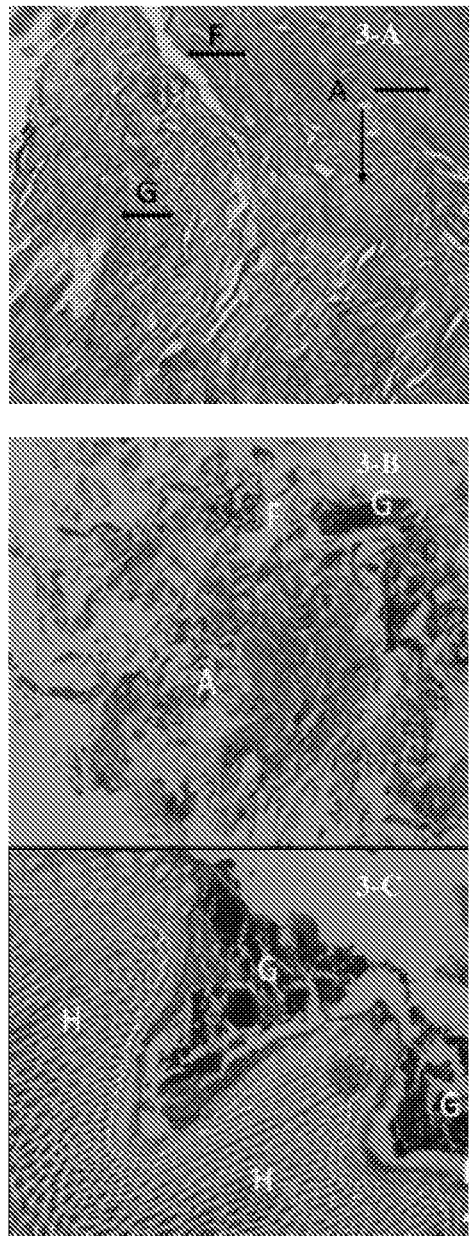
FIG. 11 corresponds to dental pulp with one year since extraction. Panel 11 (3-A) with hematoxylin eosin staining, shows fibrous tissue with different density are observed (A), with empty areas (F). No cellular nucleuses are observed. In the periphery, hyper chromatic areas, nuclear debris (G) are observed, red blood capillaries are not observed. Panel 11 (3-B) and 11 (3-C) shows disaggregation of the fibrous tissue (A) with empty areas (F), without the presence of cells or nucleus. On the periphery it shows deep blue hyper chromatic areas, highlighted in the sample (G).
Figure 12:
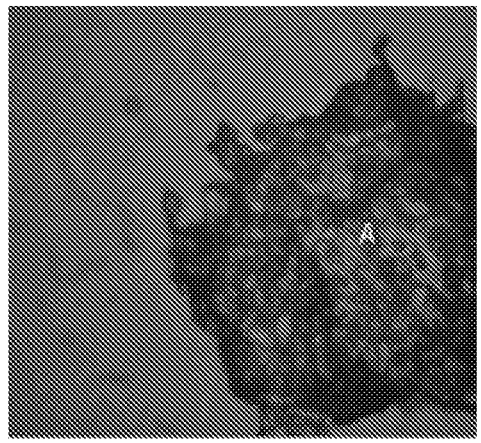
FIG. 12 corresponds to dental pulp with 20 years since extraction, shows a compacted fibrous network, nucleus, cell core structures are not observed. The network could correspond to desintegrated fibrous tissue.
Figure 13:
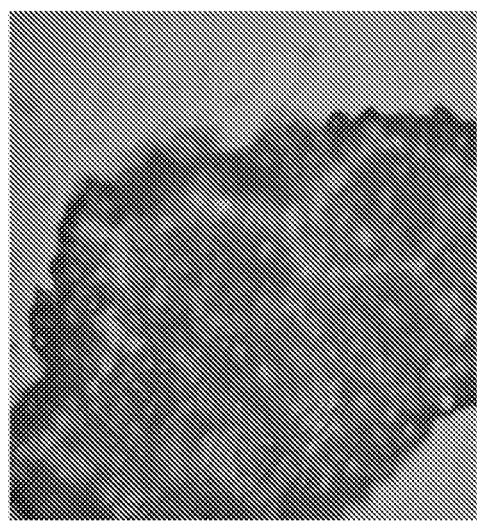
FIG. 13 corresponds to dental pulp with 40 years since extraction, shows a dense amorphous network. No presences of nuclear or cellular core structures are observed.

FIG. 8 shows the percentage of success in obtaining DNAg from pulp content and from root cement of 11 samples and the success rate in obtaining genetic profiles obtained from DNAg.

TABLE 3

Samples, description of samples, gDNA and genetic profiles obtained.

| | Time since extraction | | DNAg | | Genetic profile | | | |
| | | | | | Id plus Applied | | P Plex 21 Promega | |
| | w = weeks | | | Root | | | | |
| Code sample | m = months y = year | Gender | Pulp (ng/ul) | content (ng/ul) | Pulp | Root content | Pulp | Root content |
| 5 | 2 w | xy | 0.001 | 0.087 | 0 | +(15)xy | 0 | +(14)xy |
| 6 | 3 m | xy | 37.17 | — | +(4)(xy) | — | — | — |
| 7 | 3 m | xy | 0.005 | 0 | 0 | 0 | 0 | 0 |
| 3 | 1 y 3 m | xy | 0.284 | 0.276 | +(15)xy | +(15)xy | +(20)xy | +(20)xy |

TABLE 3-continued

Samples, description of samples, gDNA and genetic profiles obtained.

| | | | | | Genetic profile | | | |
|---|---|---|---|---|---|---|---|---|
| | Time since extraction | | DNAg | | Id plus Applied | | P Plex 21 Promega | |
| | w = weeks | | | Root | | Root | | Root |
| Code sample | m = months y = year | Gender | Pulp (ng/ul) | content (ng/ul) | Pulp | content | Pulp | content |
| 4 | 1 y 3 m | xy | 0.34 | 1.14 | +(15)xy | +(15)xy | +(20)xy | +(19)xy |
| 8 | 1 y 3 m | xy | — | 0.008 | — | −(0)(xx) | — | — |
| 2 | 18 y 1 m | xy | fracture | 0.028 | +(9)xy | — | +(12)xy | — |
| 9 | 19 y | — | 0 | 0 | — | — | 0 | 0 |
| 10 | 19 y | — | 0 | 0 | — | — | 0 | 0 |
| 11 | 22 y | xy | 0.007 | — | 0 | — | — | — |
| 1 | 38 y | xy | — | 0.002 | 0 | 0 | 0 | 0 |

—: not done
xy: gender male
xx: gender female
0: not obtained
( ): numbers in parentheses correspond to numbers of STRs.

Example 2

Morphological Analysis (Histological and Cytological Analyses)

Each sample of rehydrated pulp content was prepared for histological and cytological analyses (see FIGS. 9 to 13).

The samples for cytological analysis were placed into separate microscope slides through cell spread (smear); they were fixed with cyto spray and allowed to air dry.

An inverted optic microscope Olympus Ckx41 was used for obtaining the images of cytological analysis. The photographs were obtained with an Olympus Utv 0.5 XC-3 camera and the Micrometrics software.

The samples for histological analysis were fixed in 10% formalin Hematoxylin and eosin stain and Masson's trichrome staining were applied to the samples for histological analysis. The photographs were obtained with an Olympus Utv 0.5 XC-3 camera and the Micrometrics software.
Results.

These results allowed designing a synoptic chart of morphological markers that change in relation to post mortem interval or time since extraction (24 hours, 1 month, 1 year, 20 years and 40 years). It was possible to identify and valued some markers as nuclear cells, collagen fibers, fibroblast, etc. as shown in FIGS. 9, 10, 11, 12 and 13.

It was possible to identify some markers as nucleus, blood vessels, and/or lymphatic vessels presence, fibroblasts, and/or collagen fibers density, presence of calcifications, valued by morphometric analysis (see FIGS. 11 to 13), showing pulp samples of less than 24 hours (fresh pulp), 1 month and one year since the extraction, respectively).

The analysis of morphological changes (cytological and histological changes together) of each sample enabled its classification in different parameters for the characteristics observed in the samples from the histological and cytological analyses: presence of fibrous tissue, presence or absence of cell nucleus, blood capillaries, dentine tubules, hiperchromatic odontoblasts.

These classifications allowed the comparison of the samples with synoptic charts developed in the present invention indicating the changes observed with the time passes since dead, allowing therefore the estimation of early post mortem interval (less than 1 year), and late post mortem interval (more than 1 year), at least until 40 years of post mortem interval. In FIGS. 9 to 13 are described the parametres analyzed.

Example 3

Toxicological Analysis

A sample was selected from a teeth bank, corresponding to an animal tooth from a high environmental pollution Chilean area. The rehydrated pulp content was selected for toxicological analyses.

For detecting arsenic, the sample of rehydrated pulp content were mixed with HCl at a final concentration of 0.1 M, incubated at 37° C. during 18 hours and centrifuged at 3500 rpm during 10 minutes, pH was adjusted to ph=7.0 with NaOH 1N and the analytes were extracted in chloroform:isopropanol. The samples were dried at 70° C. during 30 minutes for further GC/MS analysis. The samples were quantified in the ZEEnit 700 P (Analytik Jena) equipment, that represents a new generation of variable compact tandem spectrometers for flame mode, hydride, HydrEA and graphite furnace technology (36)

A similar analysis technology was found in the literature for the development and validation of a gas chromatography-mass spectrometry assay for opiates and cocaine in human teeth (37)

Figure 14:
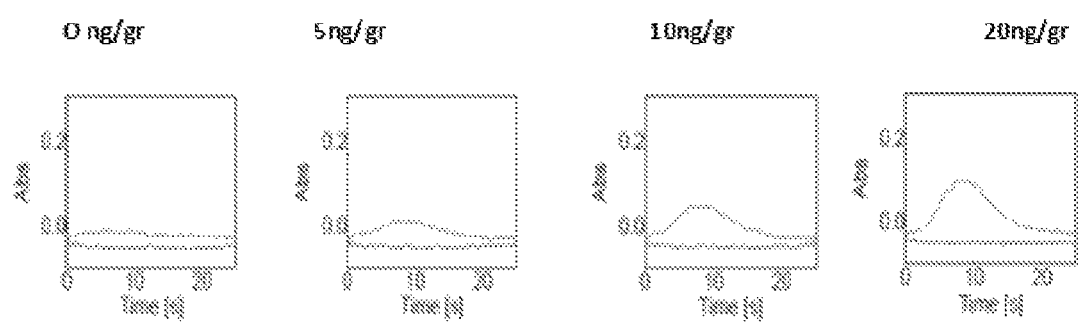
FIG. 14 shows the standard curve for arsenic concentrations at 0, 5, 10 and 20 ng/g, respectively, determined by atomic absorption spectrometry on a ZEEnit700p spectrometer.
Figure 15:
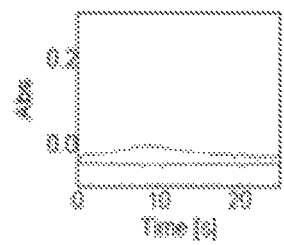
FIG. 15 shows the curve for arsenic concentrations (8.35 ng/g) in a sample obtained from animal tooth (dog), determined by atomic absorption spectrometry on a ZEEnit700p spectrometer.

FIG. 14 shows the standard curve for the identification of arsenic in the samples by atomic absorption spectrometry and FIG. 15 shows the results obtained from an animal sample measured in the same equipment, where the arsenic concentrations was 8.35 ng/g.

REFERENCES

1. H. Jiang, Z. Ju, K. L. Rudolph. Telomere shortening and ageing. Z Gerontol Geriat 40:314-324 (2007) DOI 10.1007/s00391-007-0480-0.
2. Sweet D., Hildebrand D. Recovery of DNA from human teeth by cryogenic grinding. J forensic Sci. 1998; 43(6): 1199-1202.
3. Smith B. C., Fisher D. L., Weedn V. W., Warnock G. R., Holland M. M. A systematic approach to the sampling of dental DNA. J. Forensic Sci. 1993 September; 38(5): 1194-1209.

4. Yamada Y., Yamamoto K., Yoshii T., Ishiyama I. Analysis of DNA from tooth and application to forensic dental medicine. Nihon Hoigaku Zasshi. 1989 October; 43(5): 420-423.
5. Gilbert M. T. P., Willerslev E., Hansen A. J., Barnes I., Rudbeck L., Lynnerup N., et al. Distribution patterns of postmortem damage in human mitochondrial DNA. Am. J. Hum. Genet. 2003 Ene; 72(1):32-47.
6. Woodward S. R., King M. J., Chiu N. M., Kuchar M. J., Griggs C. W. Amplification of ancient nuclear DNA from teeth and soft tissues. Pcr methods & applications. 1994; 3(4):244.
7. Carrasco P., Espinoza N., Mery A. Obtaining of DNA from dental pulps with forensic purposes. Use of AMP-FLP technique specific for APO-B locus. (Original title: Obtención de ADN de pulpas dentarias con fines de identificacion medico legal. Aplicación de la técnica AMP-FLP específica para el locus APO-B). Santiago: Dentistry Faculty, University of Chile; 1993.
8. Tran-Hung L., Tran-Thi N., Aboudharam G., Raoult D., Drancourt M. A new method to extract dental pulp DNA: application to universal detection of bacteria. PLoS ONE. 2007; 2(10):e1062.
9. Carrasco P., Barrena N. Contributions of forensic dentistry to forensic and criminological identification. Use of DNA from buccal dental tissues and fluids in forensic identification. (Original title: Aportes de la odontología forense a la identificación médico legal y criminalística. Utilización de ADN de tejidos y fluidos buco dentarios en identificación medico legal). Ediciones Juridicas de Santiago, Santiago de Chile, 2012.
10. Carrasco P., Castro A., Mery J. Thanatological forensic approach to oral maxillofacial territory, proposing a technique. (Original title: Abordaje medico legal tanatológico al territorio buco maxilofacial, proposición de una técnica). Santiago: Dentistry Faculty, University of Chile; 1992.
11. Alonso A., Martin P., Albarrán C., García P., Fernández de Simón L., Jesús Iturralde M., et al. Challenges of DNA profiling in mass disaster investigations. Croat. Med. J. 2005 Ago; 46(4):540-548.
12. Pretty I. A. Forensic dentistry: 1. Identification of human remains. Dent Update. 2007 Dic; 34(10):621-622, 624-626, 629-630.
13. Lijnen I., Willems G. DNA research in forensic dentistry. Methods Find Exp Clin Pharmacol. 2001 November; 23(9):511-517.
14. Diwaker N. R., Rajeshwari, Rao B. DNA fingerprinting. The future of forensic dentistry—a review. Indian J Dent Res. 2001 June; 12(2):81-88.
15. Malaver P. C., Yunis J. J. Different dental tissues as source of DNA for human identification in forensic cases. Croat. Med. J. 2003 June; 44(3):306-309.
16. Ricaut E, Keyser-Tracqui C., Crubezy E., Ludes B. STR-genotyping from human medieval tooth and bone samples. Forensic Sci. Int. 2005 Jun. 30; 151(1):31-35.
17. Smith B. C., Fisher D. L., Weedn V. W., Warnock G. R., Holland M. M. A systematic approach to the sampling of dental DNA. J. Forensic Sci. 1993 September; 38(5): 1194-1209.
18. Luna A. The time since death, an unresolved challenge. (Original title: La data de la muerte, un desafio no resuelto). Rev. Esp. Med. Legal. 2010; 36:47-8.
19. Henssge C. Death time estimation in case work. I. The rectal temperature time of death nomogram. Forensic Sci Int. 1988 September; 38(3-4):209-36.
20. Boy, S. C., Bernitz, H., Van Heerden, W. E P. Case Report Flow Cytometric Evaluation of Postmortem Pulp DNA Degradation American Journal of Forensic Medicine & Pathology 2003. 24: 123-127.
21. Vavpotic M., Turk T., Martincic D. S., Balazic J. Characteristics of the number of odontoblasts in human dental pulp post-mortem. Forensic Sci Int. 2009.193(1-3):122-6.
22. Caballín A., Peréa Pérez, B., De Agustín, D., Sánchez, J. Evaluation of histological pulp changes for determining the time since death. (Original title: Valoracion de los cambios histológicos pulpares para la determinación de la data de la muerte). Cient. Dent. 2010; 7 (1):9-13.
23. Ohira, H. and Yamada, Y. Advantages of dental mitochondrial DNA for detection and classification of the sequence variation using restriction fragment length polymorphisms. American Journal of Forensic Medicine and Pathology 20 (3): 261-268 September 1999.
24. Tilotta, F.; Brousseau, P.; Lepareur, E.; Yasukawa, K.; de Mazancourt, P. A comparative study of two methods of dental pulp extraction for genetic fingerprinting. Forensic Science International 202 (1-3): e39-e43 Oct. 10 2010.
25. Pinchi, V.; Torricelli, F.; Nutini, A. L.; Conti, M.; Iozzi, S.; Norelli, G. A. Techniques of dental DNA extraction: Some operative experiences. Forensic Science International 204 (1-3): 111-114 Jan. 30 2011.
26. Vasiliadis, L., Stavrianos, C., Dagkalis, P., Stavrianou, I. and Tatsis, D. Translucent Root Dentine in Relationship to Increasing Age: Review of the Literature. Research Journal of Biological Sciences 6 (2): 92-95, 2011. ISSN: 1815-8846 Medwell Journal, 2011.
27. Goedbloed M, Vermeulen M, Fang R N, Lembring M, Wollstein A, Ballantyne K, et al. Comprehensive mutation analysis of 17 Y-chromosomal short tandem repeat polymorphisms included in the AmpFISTR® Yfiler® PCR amplification kit. Int J Legal Med. 2009 3; 123(6):471-482.
28. Ruiz Linares A, Nayar K, Goldstein D B, Hebert J M, Seielstad M T, Underhill P A, et al. Geographic clustering of human Y-chromosome haplotypes. Ann Hum. Genet. 1996 September; 60(Pt 5):401-408.
29. Roewer L, Krawczak M, Willuweit S, Nagy M, Alves C, Amorim A, et al. Online reference database of European Y-chromosomal short tandem repeat (STR) haplotypes. Forensic Sci. Int. 2001 May 15; 118(2-3):106-113.
30. Takasaki T, Tsuji A, Ikeda N, Ohishi M. Age estimation in dental pulp DNA based on human telomere shortening. Int. J. Legal Med. 2003 Ago; 117(4):232-234.
31. Rees J L. Genetics of hair and skin color. Annu. Rev. Genet. 2003; 37:67-90.
32. Valverde P, Healy E, Jackson I, Rees J L, Thody A J. Variants of the melanocyte-stimulating hormone receptor gene are associated with red hair and fair skin in humans. Nat. Genet. 1995 November; 11(3):328-330.
33. Kayser M, Liu F, Janssens ACJW, Rivadeneira F, Lao O, van Duijn K, et al. Three genome-wide association studies and a linkage analysis identify HERC2 as a human iris color gene. Am. J. Hum. Genet. 2008 February; 82(2): 411-423.
34. Sturm R A, Larsson M. Genetics of human iris colour and patterns. Pigment Cell Melanoma Res. 2009 October; 22(5):544-562.
35. Hazha Star, Patrick Thevissen, Reinhilde Jacobs, Steffen Fieuws, Tore Solheim, Guy Willems. Human Dental Age Estimation by calculation of Pulp/Tooth Volume Ratios Yielded on Clinically Acquired Cone Beam Computed Tomography (CBCT) Images of Mono Radicular Teeth.

36. http://www.analytik-jena.de/en/analytical-instrumentation/products/atomic-absorption-spectrometry/flame-graphite-furnace-technique/zeenit-700-p.html
37. Pellegrini, M., Casá, A., Marchei, E., Pacifici, R., Mayné, R., Barbero, V., Garcia-Algar, O., Pichini, S. Development and validation of a gas chromatography-mass spectrometry assay for opiates and cocaine in human teeth. Journal of Pharmaceutical and Biomedical Analysis 40 (2006) 662-668.

The invention claimed is:

1. A method for forensic identification and/or estimation of post mortem interval of a subject in need thereof, wherein the method comprises the steps of: (a) obtaining a tooth; (b) taking a digital radiography of the tooth to determine the exact location of one or more access sites for (d) step perforation; (c) external rehydrating of the tooth; (d) perforating the rehydrated tooth; (e) internal rehydrating of dentin pulp complex (f) obtaining rehydrated root cement; (g) obtaining rehydrated dental pulp content; and (h) storing, preserving, processing and/or analyzing the rehydrated dental pulp content or rehydrated root cement for forensic identification and/or estimation of post mortem interval of a subject; wherein said method further comprises cleaning and sterilizing the tooth of (b) step and performing step (c) by immersing the tooth of step (b) in an external rehydration solution (ERS) for 24 to 120 hours at 37° C.

2. A method according to claim 1, wherein the tooth obtained in (a) step is a tooth from a dead body, a tooth from skeletal remains, a tooth found in a criminal scene, or any mammal tooth.

3. The method according to claim 1, wherein previous to (b) step, age determination of said subject is performed.

4. The method according to claim 3, wherein the age determination is performed by translucent root dentine.

5. The method according to claim 1, wherein from the analysis of the digital radiography taken in (b) step is calculated the distance between the pulp chamber and the occlusal face or the palatine face, and between the radicular surface and the root canal at the level of the apical third for determining and designing access or drilling for (d) step.

6. The method according to claim 1, wherein the external rehydration solution ERS comprises at least one polyol, and at least one mineral salt.

7. The method according to claim 6, wherein the at least one polyol is glycerol.

8. The method according to claim 6, wherein the external rehydration solution ERS comprises distilled sterile water, sodium bicarbonate ($NaHCO_3$), sodium phosphate heptahydrate ($Na_2HPO_4$ $7H_2O$), potassium chloride (KCl), sodium chloride (NaCl), calcium chloride ($CaCl_2$), magnesium sulfate heptahydrate ($MgSO_4.7H_2O$), and glycerol.

9. The method according to claim 6, wherein the external rehydration solution comprises: 1 L of distilled sterile water, 9 to 11 g of sodium bicarbonate ($NaHCO_3$), 6 to 8 g of sodium phosphate heptahydrate ($Na_2HPO_4$ $7H_2O$), 0.4 to 0.7 g of potassium chloride (KCL), 0.3 to 0.6 of g sodium chloride (NaCl), 0.02 to 0.06 g of calcium chloride ($CaCl_2$); 0.06 to 0.18 g of magnesium sulfate heptahydrate ($MgSO_4.7H_2O$), and 1 to 3% glycerol 100%, all in a solution buffered to ph=3.0 to 5.0.

10. Method according to claim 1, wherein in (d) step one or more perforations are made.

11. Method according to claim 10, wherein a first perforation is performed from the occlusal face to the pulp chamber when premolars or molars are used and from the palatine face to the pulp chamber when incisors or canines are used corresponding to coronary permeability and a second perforation is performed from the apical third of the root to the root canal corresponding to radicular permeability.

12. Method according to claim 1, wherein (e) step of internal rehydrating of dentin pulp complex is performed immersing the perforated tooth in an internal rehydration solution (IRS) for 24 to 96 hours.

13. Method according to claim 12, wherein the internal rehydration is performed in an incubator at 37° C. and 5% $CO_2$.

14. Method according to claim 12, wherein the internal rehydration solution (IRS) comprises mineral salts, sugars and polysaccharides, amino acids, vitamins, and nucleosides, all dissolved in a solution and buffered for maintaining pH between 7.0 and 7.2.

15. Method according to claim 14, wherein the solution contains an indicator of pH change.

16. Method according to claim 12, wherein the internal rehydration solution IRS comprises inorganic salts of calcium, magnesium, potassium and sodium in a concentration between 0.05 and 0.6 g/L, NaCl in a concentration between 6 and 7.5 g/L, glucose in a concentration between 0.8 and 1.5 g/L and hyaluronic acid in a concentration between 2 and 5 g/L, glutamine in a concentration between 0.2 and 0.35 g/L, other amino acids in concentrations between 0.01 and 0.03 g/L, vitamins in concentrations from 0.0001 to 0.005, nucleosides in concentrations between 0.005 and 0.015 g/L.

17. Method according to claim 1, wherein previous to (g) step a permeation of the chamber and the canals is made with an endodontic hand file.

18. Method according to claim 1, wherein (g) step is performed with a file mounted on a low speed vertical-vibrating contra-angle endodontic hand piece.

19. Method according to claim 18, wherein after using the file mounted on the low-speed endodontic hand piece, the file is washed with sterile distilled water for recovering the pulp content, and the tooth is placed with the crown upside down in a centrifuge tube and is centrifuged at 3000 rpm during 3 to 8 minutes at room temperature for recovering the rest of the pulp content.

20. Method according to claim 1, wherein in (h) step gDNA is obtained from rehydrated dental pulp content and rehydrated root cement.

21. Method according to claim 20, wherein the gDNA is used for determining genetic profile, gender, species, number of individuals, racial tendency, age determination and/or phenotypic profiles.

22. Method according to claim 1, wherein (h) step further comprises histological and cytological analyses, through optical microscopy of the rehydrated dental pulp content, performed for estimating post mortem interval.

23. Method according to claim 22, wherein histological and cytological results are classified in four different levels for presence or absence of cell nucleus, blood vessels, lymphatic vessels, calcifications, density of fibroblasts and collagen fibers, and cell viability, and are compared with a synoptic chart for estimating early and late post mortem interval.

24. Method according to claim 1, wherein the method enables subjecting the tooth to further analyses, or keeping it as evidence or delivering it to relatives as remains.

25. Method according to claim 1, wherein tooth can be used, wherein said tooth is selected from the group consisting of: permanent or deciduous teeth, unirradicular, birradicular or multirradicular teeth, incisors, canines, premolars or molars.

* * * * *